(12) United States Patent
Keller et al.

(10) Patent No.: US 6,458,851 B1
(45) Date of Patent: Oct. 1, 2002

(54) COMBINATIONS OF ILEAL BILE ACID TRANSPORT INHIBITORS AND CHOLESTERYL ESTER TRANSFER PROTEIN INHIBITORS FOR CARDIOVASCULAR INDICATIONS

(75) Inventors: Bradley T. Keller, Chesterfield, MO (US); James A. Sikorski, Des Peres, MO (US); Kevin C. Glenn, Maryland Heights, MO (US); Daniel T. Connolly, Ballwin, MO (US); Mark E. Smith, Webster Groves, MO (US); Joseph R. Schuh, St. Louis, MO (US)

(73) Assignee: G. D. Searle, LLC, Chicago, IL (US)

( * ) Notice: Subject to any disclaimer, the term of this patent is extended or adjusted under 35 U.S.C. 154(b) by 0 days.

(21) Appl. No.: 09/466,415

(22) Filed: Dec. 17, 1999

Related U.S. Application Data

(60) Provisional application No. 60/143,047, filed on Jul. 7, 1999, and provisional application No. 60/113,955, filed on Dec. 23, 1998.

(51) Int. Cl.[7] .................. A61K 31/4995; A61K 31/136; A61K 31/09; A61K 31/133; A61P 9/10
(52) U.S. Cl. .................. 514/655; 514/252.13; 514/718; 514/741; 514/824; 514/431; 424/451; 424/464
(58) Field of Search .................. 514/824, 741, 514/443, 252.13, 655, 718, 431; 424/451, 464

(56) References Cited

U.S. PATENT DOCUMENTS

| | | |
|---|---|---|
| 3,262,850 A | 7/1966 | Glynne |
| 3,287,370 A | 11/1966 | Mohrbacher |
| 3,389,144 A | 6/1968 | Mohrbacher |
| 3,520,891 A | 7/1970 | Mohrbacher |
| 3,674,836 A | 7/1972 | Creger |
| 3,692,895 A | 9/1972 | Nelson |
| 3,694,446 A | 9/1972 | Houlihan et al. |
| 3,714,190 A | 1/1973 | Boissier |
| 3,781,328 A | 12/1973 | Witte |
| 3,948,973 A | 4/1976 | Phillips |
| 3,962,261 A | 6/1976 | Zinnes |
| 3,972,878 A | 8/1976 | Schirmann |
| 3,983,140 A | 9/1976 | Endo |
| 4,002,750 A | 1/1977 | Ambrogi |
| 4,058,552 A | 11/1977 | Mieville |
| 4,185,109 A | 1/1980 | Rosen |
| 4,231,938 A | 11/1980 | Monaghan |
| 4,251,526 A | 2/1981 | McCall |
| 4,346,227 A | 8/1982 | Terahara |
| 4,410,629 A | 10/1983 | Terahara et al. |
| 4,444,784 A | 4/1984 | Hoffman |
| 4,448,979 A | 5/1984 | Terahara et al. |
| 4,559,332 A | 12/1985 | Grob |
| 5,075,293 A | 12/1991 | Reifschneider |
| 5,153,184 A | 10/1992 | Reifschneider |
| 5,158,943 A | 10/1992 | Sohda |
| 5,244,887 A | 9/1993 | Straub |
| 5,260,316 A | 11/1993 | Van Duzer |
| 5,334,600 A | 8/1994 | Van Duzer |
| 5,350,761 A | 9/1994 | Van Duzer |
| 5,354,772 A | 10/1994 | Kathawala |
| 5,430,116 A | 7/1995 | Kramer |
| 5,502,045 A | 3/1996 | Miettinen |
| 5,512,558 A | 4/1996 | Enhsen |
| 5,519,001 A | 5/1996 | Rampratap |
| 5,602,152 A | 2/1997 | Berthelon |
| 5,610,151 A | 3/1997 | Glombik |
| 5,663,165 A | 9/1997 | Brieaddy |
| 5,703,188 A | 12/1997 | Mandeville |
| 5,705,524 A | 1/1998 | McGee |
| 5,723,458 A | 3/1998 | Brieaddy |
| 5,767,115 A | 6/1998 | Rosenblum |
| 5,929,062 A | 7/1999 | Haines |
| 5,994,391 A | 11/1999 | Lee |
| 6,020,330 A | 2/2000 | Enhsen |
| 6,034,118 A | 3/2000 | Bischofberger |

FOREIGN PATENT DOCUMENTS

| | | |
|---|---|---|
| AU | A-30209/92 | 12/1992 |
| AU | A-61946/94 | 6/1994 |
| AU | A-61948/94 | 6/1994 |
| AU | A-61949/94 | 6/1994 |
| CA | 2025294 | 3/1991 |
| CA | 2078588 | 3/1993 |
| CA | 2085782 | 6/1993 |
| CA | 2085830 | 6/1993 |
| DE | 1211258 | 2/1968 |
| DE | 3 122 499 A1 | 12/1981 |
| DE | 196 27 430 A1 | 8/1996 |
| EP | 0 022 487 A1 | 1/1981 |
| EP | 0 067 086 | 10/1982 |
| EP | 0 129 748 | 2/1985 |
| EP | 0 033 538 B1 | 11/1985 |
| EP | 0 250 265 | 6/1987 |
| EP | 0 244 364 A2 | 11/1987 |
| EP | 0 338 331 | 6/1989 |
| EP | 0 379 161 | 1/1990 |
| EP | 0 409 281 A1 | 1/1991 |
| EP | 0 531 901 A2 | 2/1992 |
| EP | 0 508 425 A1 | 9/1992 |
| EP | 0 549 967 A1 | 12/1992 |

(List continued on next page.)

OTHER PUBLICATIONS

A. Barrett et al., "Total Synthesis and Stereochemical Assignment of the Quinquecyclopropane–Containing Cholesteryl Ester Transfer Protein Inhibitor U–106305", J. Am Chem. Soc., 1996, 118, pp. 7863–7864.

P. Barter et al. "High Density Lipoproteins and Coronary Heart Disease", Atherosclerosis, 121 1996, pp. 1–12.

*Primary Examiner*—Edward J. Webman
*Assistant Examiner*—Helen Nguyen
(74) *Attorney, Agent, or Firm*—Banner & Witcoff, Ltd.

(57) ABSTRACT

The present invention provides combinations of cardiovascular therapeutic compounds for the prophylaxis or treatment of cardiovascular disease including hypercholesterolemia, atherosclerosis, or hyperlipidemia. Combinations disclosed include an ileal bile acid transport inhibitor combined with a cholesteryl ester transfer protein (CETP) inhibitor.

8 Claims, No Drawings

FOREIGN PATENT DOCUMENTS

| | | |
|---|---|---|
| EP | 0 526 402 A1 | 2/1993 |
| EP | 0 559 064 A2 | 2/1993 |
| EP | 0 563 731 A1 | 3/1993 |
| EP | 0 568 898 A1 | 4/1993 |
| EP | 0 818 197 A1 | 6/1997 |
| EP | 0 818 448 A1 | 6/1997 |
| EP | 0 796 846 A1 | 7/1997 |
| EP | 0 801 060 A1 | 10/1997 |
| FR | 2 661 676 A1 | 2/1990 |
| GB | 1 211 258 | 11/1970 |
| GB | 2 077 264 A | 12/1981 |
| GB | 2 305 665 | 4/1997 |
| GB | 2 329 334 | 3/1999 |
| JP | 10-287662 | 10/1998 |
| WO | 89/01477 | 2/1989 |
| WO | 91/08205 | 6/1991 |
| WO | 92/17467 | 10/1992 |
| WO | 92/18115 | 10/1992 |
| WO | 92/18462 | 10/1992 |
| WO | 93/16055 | 8/1993 |
| WO | 93/21146 | 10/1993 |
| WO | 94/18183 | 8/1994 |
| WO | 94/18184 | 8/1994 |
| WO | 94/24087 | 10/1994 |
| WO | 95/21843 | 8/1995 |
| WO | 96/05188 | 2/1996 |
| WO | 96/08484 | 3/1996 |
| WO | 96/16051 | 5/1996 |
| WO | 96/40255 | 12/1996 |
| WO | 97/03953 | 2/1997 |
| WO | 97/33882 | 9/1997 |
| WO | 97/49387 | 12/1997 |
| WO | 97/49736 | 12/1997 |
| WO | 98/02432 | 1/1998 |
| WO | 98/06405 | 2/1998 |
| WO | 98/23593 | 6/1998 |
| WO | 98/35937 | 8/1998 |
| WO | 98/38182 | 9/1998 |
| WO | 98/39299 | 9/1998 |
| WO | 98/40375 | 9/1998 |
| WO | 98/56757 | 12/1998 |
| WO | 99/11259 | 3/1999 |
| WO | 99/11260 | 3/1999 |
| WO | 99/11263 | 3/1999 |
| WO | 99/14174 | 3/1999 |
| WO | 99/14204 | 3/1999 |
| WO | 99/14215 | 3/1999 |
| WO | 99/32478 | 7/1999 |
| WO | 99/35135 | 7/1999 |
| WO | 99/64409 | 12/1999 |
| WO | 00/35889 | 6/2000 |

OTHER PUBLICATIONS

A. Beckwith et al., "Iododediazoniation of Arenediazonium Salts Accompianied by Aryl Radical Ring Closure" Org. Chem. 1987, vol. 52, pp. 1922–1930.

D. Bilheimer et al., "Mevinolin and Colestipol Stimulate Receptor–Mediated Clearance of Low Density Lipoprotein From Plasma In Familial Hypercholesterolemia Heterzygotes", Proc. Natl. Acad. Sci. USA, vol. 80, Jul. 1983. pp. 4124–4128.

C. Bisgaier et al., Cholesteryl Ester Transfer Protein Inhibition By PD 140195, Lipids, vol. 29, No. 12, 1994, pp. 811–818.

D. Blankenhorn et al., "Beneficial Effects of Combined Colestipol–Niacin Therapy On Coronary Atherosclerosis and Coronary Venous Bypass Grafts", JAMA, Jun. 19, 1987, vol. 257, No. 23, pp. 3233–3240.

D. Blankenhorn et al., "Beneficial Effects of Colestipol–Niacin Therapy on the Common Carotid Artery" Circulation vol. 88, Jul. 1, 1993, pp. 20–28.

P. Bonin et al., "A Peptide Inhibitor Of Cholesteryl Ester Transfer Protein Identified By Screening a Bacteriophage Display Library", Journal of Peptide Research, 51, 1998, pp. 216–225.

G. Brown, et al., "Regression of Coronary Artery Disease As A Result of Intensive Lipid–Lowering Therapy in Men With High Levels Of Apolipoprotein B", The New England Journal of Medicine, vol. 323, Nov. 8, 1990, No. 19, pp. 1289–1339.

M. Brown et al., Induction of 3–hydroxy–3Methylglutaryl Coenzyme A Reductase Activity in Human Fibroblasts Incubated with Compactin (ML–236B), A Competitive Inhibitor of the Reductase, The Journal of Biological Chemistry, vol. 253, No. 4, Feb. 22, 1978, pp. 1121–1128.

S. Busch et al., "Cholesteryl Ester Analogs Inhibit Cholesteryl Ester But Not Triglyceride Transfer Catalyzed By The Plasma Cholesteryl Ester–Triglyceride Transfer Protein", Lipids, vol. 25, No. 4 (1990), pp. 216–220.

C. Camoutsis et al., "N–Substituted 4, 5–Dihydro–1, 2–Benzothiazepin–3–One 1, 1–Dioxide", J. Heterocyclic Chem. 17, pp. 1135–1136 (1980).

L. Cashin–Hemphill et al., "Beneficial Effects of Colestipol–Niacin on Coronary Atherosclerosis A 4–Year Follow–up", JAMA, Dec. 19, 1990, vol. 264, No. 23, pp. 3013–3017.

P. Catsoulacos et al., "Synthesis of Some N–Substituted 4,5–Dihydro–7,8–dimethoxybenzothiazepin–3–one 1,1–Dioxides", J. Heterocyclic Chem., vol. 13 (1976), pp. 1309–1314.

P. Catsoulacos et al., "Thiazo–Compounds. Dervatives of 4, 5–Dihydro–7, 8–Dimethoxybenzothiazepin–3 one 1, 1–Dioxides", Journal of Chemical and Engineering Data, vol. 22, No. 3, 1977, pp. 353–354.

K. Cho et al, "A Peptide From Hog Plasma that Inhibits Human Cholesteryl Ester Transfer Protein", Biochimica et Biophysica Acta, 1391, 1998, pp. 133–144.

D. Connolly et al., "Inactivation of Cholesteryl Ester Transfer Protein by Cysteine Modification", Biochemical and Biophysical Research Communications 223, pp. 42–47, 1996.

S. Coval et al., "Wiedendiol–A and–B, Cholesteryl Ester Transfer Protein Inhibitors From The Marine Sponge Xestosponga Wiedenmayeri", Bioorganic & Medicinal Chemistry Letter, vol. 5, No. 6, pp. 605–610, 1995.

J. Davignon et al., "Apolipoprotein E and Atherosclerosis: Quest for an APO E Receptor Defect Leads to the Discvery of Pseudo Type III Dyslipoproteinemia in a Family", Atherosclerosis IX, pp. 199–203.

J. Davignon et al., "Comparative Efficacy and Saftety of Provastatin, Nicotinic Acid and The Two Combined in Patients with Hypercholesterolemia", The AMerican Jopurnal of Cardioology, Feb. 15, 1994, pp. 339–345.

C. East et al., "Combination Drug Therapy for Familial Combined Hyperlipidemia", Annals of Internal Medicine, Jul. 1, 1988, pp. 25–32.

J. Emmerich et al., "Efficacy and Safety of Simvastatin (Alone or in Association with Cholestyramine) A 1 yr. Study in 66 Patients with Type II Hyperlipoproteinaemia", European Heart Journal (1990), 11, pp. 149–155.

D. Erkelens, "Combination Drug Therapy with HMG Co A Reductase Inhibitors and Bile Acid Sequestrants for Hypercholesterolmia", Cardiology, 1990, 77, (suppl 4). pp. 33–38.

H. Ginsberg, "Update on the Treatment of Hypercholesterolemia with a Focus on HMG–CoA Reductase Inhibitors and Combination Regimens", Clinical Cardiology 18, pp. 307—315, (1995).

C. Glueck et al., "Gemfibrozil–Lovastatin Therapy for Primary Hyperlipoproteinemias" The American Journal of Cardiology, Jul. 1, 1992, vol. 70, No. 1, pp. 1–9.

S. Grundy et al., "Influence of Combined Therapy with Mevinolin and Interruption of Bile–Acid Reabsorption on Low Density Lipoproteins in Heterozygous Familial Hypercholesterolemia", Annals of Internal Medicine, 1985, 103: pp. 339–343.

H. Gylling et al., "Effects Of Inhibiting Cholesterol Absorption And Synthesis On Cholesterol And Lipoprotein Metabolism In Hypercholesterolemic Non–Insulin–Dependent Diabetic Men", Journal of Lipid Research, vol. 37, 1996, pp. 1776–1785.

E. Haber, "Molecular Cardiovascular Medicine" Scientific American, pp. 35–40.

V. Hegde et al., "A Depsipeptide Fungal Metabolite Inhibitor Of Cholesteryl Ester Transfer Protein", Bioorganic & Medicinal Chemistry Letters 8, 1998, pp. 1277–1280.

L.Hellberg et al., "5a–Hydroxy–3a–Cholestanecarboxylic" The New Journal for Organic Synthesis, vol. 15, No. 1–2, Feb.–Apr. 1983, pp. 154–156.

J. Heubi et al., "Primary Bile Acid Malabsorption: Defective In Vitro Ileal Active Bile Acid Transport", Gastroenterology 1982, 83: pp. 804–811.

N. Hoogerbrugge et al., "The Additional Effects of Acipimox To Simvastatin In The Treatment of Combined Hyperlipidaemia", Journal of Internal Medicine, 1997, 241: pp. 151–155.

N. Hoogerbrugge et al., "The Effacy and Safety of Pravastatin Compared To And In Combination With Bile Acid Binding Resins, In Familial Hypercholesterolaemia", Journal of Internal Medicine 1990, 228; pp. 261–266.

A. Hutchesson et al., "Dual Bezafibrate–Simvastatin Therapy For Combined Hyperlipidaemia", Journal of Clinical Pharmacy and Therapeutics 1994, 19, 387–389.

T. Ichihashi, "Mechanism of Hypocholesterolemic Action of S–8921 in Rats: S–8921 Inhibits Ileal Bile Acid Absorption", The Journal Of Pharmacology And Experimental Therapeutics, vol. 284, No. 1, pp. 43–50.

D. Illingworth, et al., "Influence of Lovstatin plus Gemfibrozil on Plasma Lipids and Lipoproteins in Patents With Heterozygous Familial Hypercholesterolemia", Circulation vol. 79, No. 3, Mar. 1989, 590–596.

D. Illingworth, "Mevinolin Plus Colestipol in Therapy for Severe Heterozygous Familial Hypercholesterolemia", Annalos of Internal Medicine, 1984; 101, pp. 598–604.

International Search Report mailed May 23, 2000 based on PCT/US 99/27942.

International Search Report mailed May 23, 2000 based on PCT/US 99/27943.

International Search Report mailed May 23, 2000 based on PCT/US 99/27944.

International Search Report mailed May 23, 2000 based on PCT/US 99/27945.

International Search Report mailed May 18, 2000 based on PCT/US 99/27947.

International Search Report mailed May 15, 2000 based on PCT/US 99/27948.

International Search Report mailed May 17, 2000 based on PCT/US 99/27949.

J. Kane, et al., "Regression of Coronary Atherosclerosis During Treatment of Familial Hypercholesterolemia With Combined Drug Regimens", JAMA, Dec. 19, 1990, Chapter 26, vol. 264, No. 23, pp. 3007–3012.

A. Katritzky et al., "Preparation Of 6–7– And 8–Membered Sultams By Friedel–Crafts Cyclization Of w–Phenylalkanesulfamoyl Chlorides", Organic Preparations and Procedures Int., 24 (4), pp. 463–467 (1992).

T. Kazumi et al., "Effects of Niceritrol On Elevated Serum Lipoprotein LP (A) Levels in Diabetic Patients With Or Without Overt Proteinuria", Current Therapeutic Research, vol. 55, No. 5, May 1994, pp. 546–551.

W. Kramer, et al., "Intestinal Bile Acid Absorption", The Journal of Biological Chemistry. vol. 268, No. 24 Issue of Aug. 25, pp. 18035–18046, 1993.

Kuo, M.S. et al., "Discovery, Isolation, Structure Elucidation, and Biosynthesis of U–106305, a Choresteryl Ester Transfer Protein Inhibitor from UC 11136", J. Am. Chem. Soc. 117, pp. 10629–10634 (1995).

Kvis, K. et al., "Benzocycloheptenes and Heterocyclic Analogues as Potential Drugs. VII, 4–Phenyl–,3,4, 5–Tetrahydro–1–Benzothiepins and Some Related Compounds", Chem. Commun./Vo.37/(1973) pp. 3808–3816.

Lee, J.C. et al., "A Cholesteryl Ester Transfer Protein Inhibitor from an Insect–associated Fungus", The Journal of Antibiotics 49(7), pp. 693–696.

A.M. Lees et al., "Therapy of Hypercholesterolemia With Mevinolin And Other Lipid–Lowering Drugs", Arteriosclerosis 6, 1986, p. 544a.

T. Leren et al., "Effects of Lovastatin Alone and In Combination with Cholestyramine on Serum Lipids and Apolipoproteins in Heterozygotes for Familial Hypercholesterolemia", International Journal for Research and Investigation on Atherosclerosis and Related Dieseases, 73, (1988), pp. 135–141.

M. Lewis, et al., Effects Of 2164U90 on Ileal Bile Acid Absorption and Serum Cholesterol in Rats and Mice, Journal of Lipid Research, vol. 36, 1995,pp. 1098–1105.

R. Lewis, Hawley's Condensed Chemical Dictionary, p. 1238.

W. Ling et al., "Minireview Dietary Phytosterols A Review of Metabolism, Benefits and Side Effects", Life Sciences, vol. 57, No. 3, 1995, pp. 195–206.

H. Mabuchi et al., "Reduction of Serum Cholesterol In Heterozygous Patients with Familial Hypercholesterolemia", The New England Journal of Medicine, vol. 308, Mar. 17, 1983,pp. 609–613.

M. Malloy et al., "Complementarity of Colestipol, Niacin, and Lovastatin in Treatment of Servere Familial Hypercholesterolemia", Annals of Internal Medicine 1987; 107: pp. 616–623.

W. Mandeville et al., Bile Acid Sequestrants: Their Use In Combination With Other Lipid–Lowering Agents, Idrugs 1999 vol. 2., No. 3, pp. 237–242.

G. Marais et al., "Rhabdomyolysis and Acute Renal Failure Induced by Combination Lovastatin and Gemfibrozil Therapy", Annals of Internal Medicine, Feb. 1, 1990, vol. 112, No. 3, pp. 228–230.

P. McCarthy, "New Approaches to Atherosclerosis: An Overview", Medicinal Research Reviews, vol. 13, No. 2, 1993, pp. 139–159.

R. Morton, Regulation of Lipid Transfer Between Lipoproteins By An Endogenous Plasma Protein: Selective Inhibition Among Lipoprotein Classes, Journal of Lipid Research, vol. 35, 1994, pp. 836–847.

F. Nerdel et al., "Quartermay Salts of B–Amino Aldehydes and B–Iodoaldehydes", Chemische Berichte (Ed. H. Zahn), vol. 98 (1965), pp. 728–734.

M. Newman et al., "The Conversion of Phenols to Thiophenols via Dialkylthiocarbamates", The Journal Of Organic Chemistry, vol. 31, Sep.–Dec. 1966, pp. 3980–3984.

A. Orahovats et al., "A Ring Enlargement from Seven–to Ten–Membered–Ring Sulfonamide Derivatives", Helvetica Chimica Acta, vol. 79, (1996), pp. 1121–1128.

H. Pan et al., "Pharmacokinetics and Pharmacodynamics of Pravastatin Alone and With Cholestyramine in Hypercholesterolemia", Clin. Pharmacol Ther. (1980) 9, 313, pp. 201–207.

N. Panagiotopoulos et al., "N(P–Bromophenyl)—4,5—Dihydro—7,8—Dimethoxy Benzothiazepine—ONE 1, 1–Dioxide C17 H16 brNO5S", Cryst. Struct. Comm. (1980) 9, pp. 313–319.

R. Pasternak et al., "Effect of Combination Therapy with Lipid–Reducing Drugs in Patients with Coronary Heart Disease and "Normal" Cholesterol Levels", Annals of Internal Medicine, Oct. 1, 1996, vol. 125, No. 7, pp. 529–538.

R. Patra et al., "Conformational and Steric Requirements Of The Side Chain For Sulphur Participation In Benzthiepin Derivatives", Tetrahedron Letters, vol. 30, No. 32, pp. 4279–4282, 1989.

R. Pierce et al., Myopathy and Rhabdomyolysis Associated With Lovastatin–Gemfibrozil Combination Therapy, JAMA, Jul. 4, 1990, vol. 264, No. 1, pp. 71–75.

W. Pirkle et al., "Trichlorosilane–Induced Cleavage. A Mild Method for Retrieving Carbinols From Carbamates", Jouranal Organic Chemistry, vol. 42, No. 15, 1977, pp. 2781–2782.

W. Pirkle et al., "Dynamic NMR Studies of Disatereomeric Carbamates: Implications toward the Determination of Relative Configuration by NMR" Journal of Organic Chemistry, vol. 44, No. 26, 1979, pp. 4891–4896.

W. Pirkle et al., "An Example of Automated Liquid Chromatography Synthesis of a Broad–Spectrum Resolving Agent and Resolution of 1–(Naphthyl) 2, 2, 2–Trifluroethanol", The Journal of Organic Chemistry vol. 39, No. 26, 1974, pp. 3904–3906.

T. Pietzonka et al., "Phosphonate–Containing Analogs Of Cholesteryl Ester As Novel Inhibitors Of Cholesteryl Ester Transfer Protein", Bioorganic & Medicinal Chemistry Letters, vol. 6, No. 16, pp. 1951–1954.

Pravastatin Multicenter Study Group II, "Comparative Efficacy and Safety of Pravastatin and Cholestyramine Alone And Combined in Patients With Hypercholesterolemia", Archives of Internal Medicine, vol. 153, Jun. 14, 1993, pp. 1321–1328.

E. Reihner et al., Regulation of Hepatic Cholesterol Metabolism In Humans: Stimulatory Effects of Cholestyramine on HMG–CoA Reductase Activity and Low Denisity Lipoprotein Receptor Expression In Gallstone Patients, Journal of Lipid Research, vol. 31, 1990, pp. 2219–2226.

R. Remick et al., "Comparision of Fluoxetine and Desipramine In Depressed Outpatients", Therapeutic Research, vol. 53, No. 5, May 1993, pp. 457–483.

S. Rosenblum et al., Discovery of 1–(4–Fluorophenyl)–(3R)–[3–(4–fluorophenyl)–(3S)–hydroxypropyl]–(4S)–(4–hydroxyphenyl)–2–azetidinone (SCH 58235): A Designed, Potent, Orally Active Inhibitor of Cholesterol Absorption, Journal of Medicinal Chemistry, 1998, vol. 41, No. 6, pp. 973–980.

G. Salem et al., "Benzothiazine and Benzothizepine Derivatives: Structures of N–p–Bromophenyl–6, 7–Dimethoxy–1, 2–Benzothiazin–3(4H)–One 1, 1–Dioxide (BBTZ) and 4, 5–Dihydro–8,9–Dimethoxy–N–(5–Methyl–2–Pyridyl)–1, 2–Benzothiazepin–3–One 1, 1–Dioxide (MPTE)" Acta Cryst. (1986) C42, pp. 1581–1584.

J. Sasaki et al., "Effects of Fluvastatin, A New Inhibitor of HMG–CoA Reductase, and Niceritol on Serum Lipids, Lipoproteins and Cholesterol Ester Transfer Activity In Primary Hypercholesterolemic Patients", International Journal of Clinical Pharmacology and Therapeutics, vol. 33, No. 7, 1995, pp. 420–426.

K. Sindelar et al., Neurotropic and Psykotropic Compounds. XXIX. Derivatives Of 2,3,4, 5–Tetrahydro–1–Benzothiepin, Chemical Commun., vol. 33, 1968, pp. 4315–4327.

K. Sindelar et al., Benzocycloheptenes and Hete 1 rocyclic Analogues As Potential Drugs. III. Further Synthetic Experiments In The Series Of 1–Benzothiepin Derivatives, vol. 37, 1972, 1195–1206.

C. Sirtori, "New Targets For Lipid Lowering And Atherosclerosis Prevention", Pharmac. Ther. vol. 67, No. 3., pp. 433–447, 1995.

Y. Son, "Purification and Characterization of Human Plasma Proteins That Inhibit Lipid Transfer Activities", Biochimica et Biophysica Acta, 795, 1984, pp. 473–480.

D. Sprecher et al., "Low–Dose Combined Therapy with Fluvastin and Cholestyramine in Hyperlipidemic Patients", Ann Intern Med. 1994; 120: pp. 537–543.

C.I. Stassinopoulou, et al., "C NMR Spectra of Benzothiazepinone, Benzothiazinone and Benzosulphonamide N–Substituted Dervatives" Department of Biology, Nuclear Research Center.

E. Stedronsky et al., "Interaction of Bile Acids and Cholesterol with Non–Systemic Agents Having Hypocholesterolemic Properties", Biochimica et Biophysica Acta., 1210, 1994, pp. 255–287.

I. Stein, et al., "Effects of Simvastatin and Cholestyramine in Familial and Nonfamilial Hypercholesterolemia", Arch Intern Med. vol. 150, Feb. 1990, pp. 341–345.

E. Stein et al., "Lovastatin Alone And In Combination For Treatment Of Primary Hypercholesterolema", Alan R. Liss, Inc. 1988, pp. 281–293.

K. Suckling, et al., Cholesterol Lowering and Bile Acid Excretion in the Hamster with Cholestyramine Treatment, Atherosclerosis, 89, (1991) pp. 183–190.

T. Swenson, "Mechanism of Cholesteryl Ester Transfer Protein Inhibition by a Neutralizing Monoclonal Antibody and Mapping of the Monoclonal Antibody Epitope", The Journal of Biological Chemistry, vol. 264, No. 24, Aug. 25, pp. 14318–14326, 1989.

A. Tall, "Plasma Cholesteryl Ester Transfer Protein", Journal of Lipid Research, vol. 34, 1993, pp. 1255–1274.

Y. Tamura et al., Novel Conversions of Benzo [b] thiophen–3 (2–H)–ones into 1,2–Benzisothiazole and Tetrahydro–1, 2–Benzothiazepin–5–One Systems via Sulphimide Intermediates, J.C.S. Perkin I, pp. 2830–2834.

K. Thurmond et al., "Water–Soluble Knedel–like Structures: The Preparation of Shell–Cross–Linked Small Particles", Journal American Chemistry Soc. vol. 118, No. 30, 1996, pp. 7239–7240.

P. Tyle, "Iontophoretic Devices for Drug Delivery", Pharmaceutical Research, vol. 3. No. 6 1986, pp. 318–325.

M. Une et al., Metabolism of 3a, 7a–Dihydroxy–7b–Methyl–5b–Cholanoic Acid and 3a, 7B–Dihydroxy–7a–Methyl–5B–Cholanoic Acid Hamsters, Biochimica et Biophysica Acta, 833 (1985), pp. 196–202.

J. Vacek et al., Comparison of Lavastatin (20 mg) and Nicotinic Acid (1.2g) With Either Drug Alone for Type II Hyperlipoproteinemia, The American Journal Of Cardiology, vol. 76, Jul. 15, 1995, pp. 182–184.

M. Van Heek et al., "In Vivo Metabolism–Based Discovery of a Potent Cholesterol Absorption Inhibitor, SCH58235, in the Rat and Rhesus Monkey Through the Identification of the Active Metabolities of SCH48461", The Journal of Pharmacology and Expermental Therapeutics, vol. 283, No. 1, pp. 157–754.

G. Vega et al., "Treatment of Primary Moderate Hypercholesterolemia With Lovastatin (Mevinolin) and Colestipol", JAMA, Jan. 2, 1987, vol. 257, No. 1, pp. 33–37.

G. Wess et al., "Synthesis and Biological Activity of Bile Acid–Derived HMG–CoA Reductase Inhibitors. The Role of 21–Methyl in Recognition of HMG–CoA Reductase and the IIeal Bile Acid Transport System", Journal Of Medicinal Chemistry 1994, 37, pp. 3240–3246.

J. Wetterau et al., "An MTP Inhibitor that Normalizes Atherogenic Lipoprotein Levels In WHHL Rabbits", Science vol. 282, Oct. 23, 1998, pp. 751–754.

O. Wiklund et al., "Pravastatin and Gemfibrozil Alone and in Combination for the Treatment of Hypercholesterolemia", The American Journal of Medicine vol. 94, Jan. 1993, pp. 13–19.

S. Wirebaugh et al., "A Retrospective Review of the Use of Lipid–Lowering Agents in Combination, Specifically, Gemfibrozil and Lovastatin", Pharmacotherapy vol. 12, No. 6, 1992, pp. 445–450.

J. Witztum, "Drugs Used In the Treatment of Hyperlipoproteinemias", The Pharmacological Basis of Therapeutics, $9^{th}$ Edition, pp. 875–894.

Yan Xia et al., "Substituted 1,3,5–Triazines As Cholesteral Ester Transfer Protein Inhibitors", Bioorganic & Medicinal Chemistry Letters, vol. 6, No. 7, 1996, pp. 919–922.

A. Yamamoto et al., "Effects of Probucol on Xanthomata Regression in Familial Hypercholesterolemia", Am Journal Cardiolgy, 1986, 57: pp. 29H–35H.

K. Ytre–Arne et al., "Simvastatin and Cholestyramine In the Long–Term Treatment of Hypercholesterolaemia", Journal of Internal Medicine (1989): 226, pp. 285–290.

Angelin, B., "Regulation of Hepatic Cholesterol Metabolism in Man," Ann. Med. 23, pp. 10–27 (1991).

Blum, C. B., "Comparison of Properties of Four Inhibitors of 3–Hydroxy–3–Methylglutaryl–Coenzyme A Reductase," Am. J. Cardiol., 73(14), 3D–11D, (1994).

Cayen, M.N., "Dispositi9n, Metabolism and Pharmacokinetics of Anthyperlipedemic Agents in Laboratory Animals and Man," Pharmac. & Ther., 29, pp. 157–204 (1985).

Da Col, et al., "Tolerability and Efficacy of Combination Therapy with Simvastatin Plus Gemfibroail in Type II Refractory Familial Combined Hyperlipidemia," Curr. Therap. Research, vol. 53, No. 5, pp. 473–483 (1993).

Davignon, et al. "HMG CoA Reductase Inhibitors: A look back and a look ahead," Can. J. Cardiol., 8(8), pp. 843–864 (1992).

Endo, A. "Chemistry, biochemistry and pharmacology of HMG–Co–A reductase inhibitors," Klin. Wochemschr. 66, pp. 421–427 (1988).

Kramer et al., "Bile acid derived HMG–CoA reductase inhibitors," Biochimica dt Biophysica Acta, 1227 pp. 137–154 (1994).

Marcus, A., "Role of the HMG–CoA Reductase Inhibitors in the Treatment of Dyslipidemia: An Evolutionary Review," CVR&R, pp. 13–27 (Jan. 1996).

COMBINATIONS OF ILEAL BILE ACID TRANSPORT INHIBITORS AND CHOLESTERYL ESTER TRANSFER PROTEIN INHIBITORS FOR CARDIOVASCULAR INDICATIONS

This application claims priority of U.S. provisional application Ser. No. 60/143,047 filed Jul. 7, 1999 and of U.S. provisional application Ser. No. 60/113,955 filed Dec. 23, 1998.

BACKGROUND OF THE INVENTION

1. Field of the Invention

The present invention relates to methods of treating cardiovascular diseases, and specifically relates to combinations of compounds, compositions, and methods for their use in medicine, particularly in the prophylaxis and treatment of hyperlipidemic conditions such as are associated with atherosclerosis, hypercholesterolemia, and other coronary artery disease in mammals. More particularly, the invention relates to ileal bile acid transporter (IBAT) inhibiting compounds. The invention also relates to cholesteryl ester transfer protein (CETP) activity inhibiting compounds.

2. Description of Related Art

It is well-settled that hyperlipidemic conditions associated with elevated concentrations of total cholesterol and low-density lipoprotein (LDL) cholesterol are major risk factors for coronary heart disease and particularly atherosclerosis. Since high levels of LDL cholesterol increase the risk of atherosclerosis, methods for lowering plasma LDL cholesterol would be therapeutically beneficial for the treatment of atherosclerosis and other diseases associated with accumulation of lipid in the blood vessels. These diseases include, but are not limited to, coronary heart disease, peripheral vascular disease, and stroke.

Atherosclerosis underlies most coronary artery disease (CAD), a major cause of morbidity and mortality in modern society. High LDL cholesterol (above about 180 mg/dl) and low HDL cholesterol (below 35 mg/dl) have been shown to be important contributors to the development of atherosclerosis. Other diseases or risk factors, such as peripheral vascular disease, stroke, and hypercholesterolaemia are negatively affected by adverse HDL/LDL ratios.

Interfering with the recirculation of bile acids from the lumen of the intestinal tract is found to reduce the levels of serum cholesterol in a causal relationship. Epidemiological data has accumulated which indicates such reduction leads to an improvement in the disease state of atherosclerosis. Stedronsky, in "Interaction of bile acids and cholesterol with nonsystemic agents having hypocholesterolemic properties," *Biochimica et Biophysica Acta,* 1210, 255–287 (1994) discusses the biochemistry, physiology and known active agents surrounding bile acids and cholesterol.

Transient pathophysiologic alterations are shown to be consistent with interruption of the enterohepatic circulation of bile acids in humans with an inherited lack of IBAT activity, as reported by Heubi, J. E., et al. See "Primary Bile Acid Malabsorption: Defective in Vitro Ileal Active Bile Acid Transport", *Gastroenterology,* 83, 804-11 (1982).

In another approach to the reduction of recirculation of bile acids, the ileal bile acid transport system is a putative pharmaceutical target for the treatment of hypercholesterolemia based on an interruption of the enterohepatic circulation with specific transport inhibitors (Kramer, et al., "Intestinal Bile Acid Absorption" *The Journal of Biological Chemistry,* 268 (24), 18035–46 1993).

In several individual patent applications, Hoechst Aktiengesellschaft discloses polymers of various naturally occurring constituents of the enterohepatic circulation system and their derivatives, including bile acid, which inhibit the physiological bile acid transport with the goal of reducing the LDL cholesterol level sufficiently to be effective as pharmaceuticals and, in particular for use as hypocholesterolemic agents. The individual Hoechst patent applications which disclose such bile acid transport inhibiting compounds are each separately listed below.

R1. Canadian Patent Application No. 2,025,294.

R2. Canadian Patent Application No. 2,078,588.

R3. Canadian Patent Application No. 2,085,782.

R4. Canadian Patent Application No. 2,085,830.

R5. EP Application No. 0 379 161.

R6. EP Application No. 0 549 967.

R7. EP Application No. 0 559 064.

R8. EP Application No. 0 563 731.

Selected benzothiepines are disclosed in world patent application number WO 93/321146 for numerous uses including fatty acid metabolism and coronary vascular diseases.

Other selected benzothiepines are known for use as hypolipaemic and hypocholesterolaemic agents, especially for the treatment or prevention of atherosclerosis as disclosed in application No. EP 508425. A French patent application, FR 2661676 discloses additional benzothiepines for use as hypolipaemic and hypocholesterolaemic agents. Furthermore, patent application no. WO 92/18462 lists other benzothiepines for use as hypolipaemic and hypocholesterolaemic agents. U.S. Pat. No. 5,994,391 (Lee et al.) Each of the benzothiepine hypolipaemic and hypocholesterolaemic agents described in these individual patent applications is limited by an amide bonded to the carbon adjacent the phenyl ring of the fused bicyclobenzothiepine ring.

Further benzothiepines useful for the treatment of hypercholesterolemia and hyperlipidemia are disclosed in patent application no. PCT/US95/10863. More benzothiepines useful for the prophylaxis and treatment of hypercholesterolemia and hyperlipidemia as well as pharmaceutical compositions of such benzothiepines are described in PCT/US97/04076. Still further benzothiepines and compositions thereof useful for the prophylaxis and treatment of hypercholesterolemia and hyperlipidemia are described in U.S. Application Ser. No. 08/816,065.

In vitro bile acid transport inhibition is disclosed to correlate with hypolipidemic activity in The Wellcome Foundation Limited disclosure of the patent application No. WO 92/16055 for "Hypolipidemic Benzothiazepine Compounds." That publication describes a number of hypolipidemic benzothiazepine compounds. Additional hypolipidemic benzothiazepine compounds (particularly 2,3,4,5-tetrahydrobenzo-1-thi-4-azepine compounds) are disclosed in patent application No. WO 96/05188. A particularly useful benzothiazepine disclosed in WO 96/05188 is the compound of formula B-2. Further hypolipidemic benzothiazepine compounds are described in patent application No. WO 96/16051.

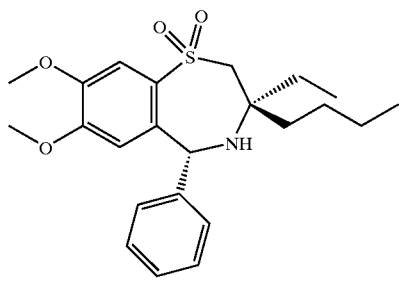

(3R,5R)-3-butyl-3-ethyl-2,3,4,5-tetrahydro-,7,8-dimethoxy-5-phenyl-1-4-benzothiazepine 1,1-dioxide Other benzothiazepine compounds useful for control of cholesterol are described in PCT Patent Application No. WO 99/35135. Included in that description is the compound of formula B-7.

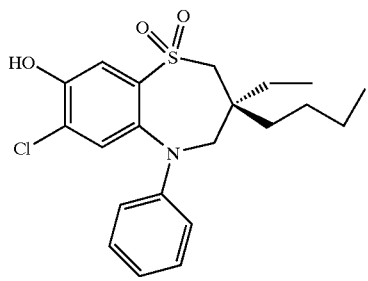

Further IBAT inhibitor compounds include a class of naphthalene compounds, described by T. Ichihashi et al. in *J. Pharmacol. Exp. Ther.*, 284(1), 43–50 (1998). In this class, S-8921 (methyl 1-(3,4-dimethoxyphenyl)-3-(3-ethylvaleryl)-4-hydroxy-6,7,8-trimethoxy-2-naphthoate) is particularly useful. The structure of S-8921 is shown in formula B-20. Further naphthalene compounds or lignin derivatives useful for the treatment or prophylaxis of hyperlipidemia or atherosclerosis are described in PCT Patent Application No. WO 94/24087.

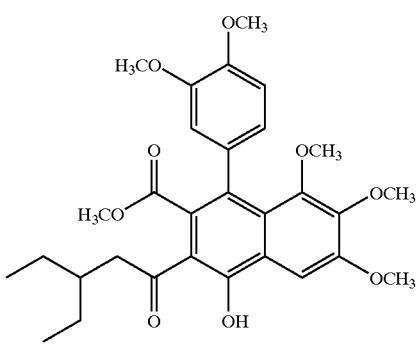

Inhibition of cholesteryl ester transfer protein (CETP) has been shown to effectively modify plasma HDL/LDL ratios, and is expected to check the progress and/or formation of certain cardiovascular diseases. CETP is a plasma protein that facilitates the movement of cholesteryl esters and triglycerides between the various lipoproteins in the blood (Tall, *J. Lipid Res.*, 34, 1255-74 (1993)). The movement of cholesteryl ester from HDL to LDL by CETP has the effect of lowering HDL cholesterol. It therefore follows that inhibition of CETP should lead to elevation of plasma HDL cholesterol and lowering of plasma LDL cholesterol, thereby providing a therapeutically beneficial plasma lipid profile. Evidence of this effect is described in McCarthy, *Medicinal Res. Revs.*, 13, 139-59 (1993). Further evidence of this effect is described in Sitori, *Pharmac. Ther.*, 67, 443-47 (1995)). This phenomenon was first demonstrated by Swenson et al., (*J. Biol. Chem.*, 264, 14318 (1989)) with the use of a monoclonal antibody that specifically inhibits CETP. In rabbits, the antibody caused an elevation of the plasma HDL cholesterol and a decrease in LDL cholesterol. Son et al. (*Biochim. Biophys. Acta*, 795, 743-480 (1984)) describe proteins from human plasma that inhibit CETP. U.S. Pat. No. 5,519,001, herein incorporated by reference, issued to Kushwaha et al., describes a 36 amino acid peptide derived from baboon apo C-1 that inhibits CETP activity. Cho et al. (*Biochim. Biophys. Acta* 1391, 133–144 (1998)) describe a peptide from hog plasma that inhibits human CETP. Bonin et al. (J. Peptide Res., 51, 216–225 (1998)) disclose a decapeptide inhibitor of CETP. A depspeptide fungal metabolite is disclosed as a CETP inhibitor by Hedge et al. in *Bioorg. Med. Chem. Lett.*, 8, 1277–80 (1998).

There have been several reports of non-peptidic compounds that act as CETP inhibitors. Barrett et al. (*J. Am. Chem. Soc.*, 188, 7863–63 (1996)) describe cyclopropane-containing CETP inhibitors. Further cyclopropane-containing CETP inhibitors are described by Kuo et al. (*J. Am. Chem. Soc.*, 117, 10629–34 (1995)). Pietzonka et al. (*Bioorg. Med. Chem. Lett.*, 6, 1951–54 (1996)) describe phosphonate-containing analogs of cholesteryl ester as CETP inhibitors. Coval et al. (*Bioorg. Med. Chem. Lett.*, 5, 605–610 (1995)) describe Wiedendiol -A and -B, and related sesquiterpene compounds as CETP inhibitors. Lee et al. (*J. Antibiotics*, 49, 693–96 (1996)) describe CETP inhibitors derived from an insect fungus. Busch et al. (*Lipids*, 25, 216–220, (1990)) describe cholesteryl acetyl bromide as a CETP inhibitor. Morton and Zilversmit (*J. Lipid Res.*, 35, 836–47 (1982)) describe that p-chloromercuriphenyl sulfonate, p-hydroxymercuribenzoate and ethyl mercurithiosalicylate inhibit CETP. Connolly et al. (*Biochem. Biophys. Res. Comm.*, 223, 42–47 (1996)) describe other cysteine modification reagents as CETP inhibitors. Xia et al. describe 1,3,5-triazines as CETP inhibitors (*Bioorg. Med. Chem. Lett.*, 6, 919–22 (1996)). Bisgaier et al. (*Lipids*, 29, 811–8 (1994)) describe 4-phenyl-5-tridecyl-4H-1,2,4-triazole-thiol as a CETP inhibitor. Additional triazole CETP inhibitors are described in U.S. patent application Ser. No. 09/153,360, herein incorporated by reference. Sikorski et al. disclosed further novel CETP inhibitors in PCT patent application No. WO 9914204.

Substituted 2-mercaptoaniline amide compounds can be used as CETP inhibitors and such therapeutic compounds are described by H. Shinkai et al. in PCT Patent Application No. WO 98/35937.

Some substituted heteroalkylamine compounds are known as CETP inhibitors. In European Patent Application No. 796846, Schmidt et al. describe 2-aryl-substituted pyridines as cholesterol ester transfer protein inhibitors useful as cardiovascular agents. One substituent at $C_3$ of the pyridine ring can be an hydroxyalkyl group. In European Patent Application No. 801060, Dow and Wright describe heterocyclic derivatives substituted with an aldehyde addition product of an alkylamine to afford 1-hydroxy-1-amines. These are reported to be β3-adrenergic receptor agonists useful for treating diabetes and other disorders. In Great Britain Patent Application No. 2305665, Fisher et al. disclose 3-agonist secondary amino alcohol substituted pyridine derivatives useful for treating several disorders including cholesterol levels and atherosclerotic diseases. In European Patent Application No. 818448 (herein incorporated by reference), Schmidt et al. describe tetrahydroquinoline derivatives as cholesterol ester transfer protein inhibitors. European Patent Application No. 818197, Schmek et al. describe pyridines with fused heterocycles as cholesterol ester transfer protein inhibitors. Brandes et al. in German Patent Application No. 19627430 describe bicyclic condensed pyridine derivatives as cholesterol ester transfer protein inhibitors. In PCT Patent Application No. WO 9839299, Muller-Gliemann et al. describe quinoline derivatives as cholesteryl ester transfer protein inhibitors.

Polycyclic compounds that are useful as CETP inhibitors are also disclosed by A. Oomura et al. in Japanese Patent No. 10287662. For example, therapeutic compounds having the structures C-1 and C-8 were prepared by culturing Penicillium spp.

Cycloalkylpyridines useful as CETP inhibitors are disclosed by Schmidt et al. in European Patent No. EP 818448. For example, the therapeutic compound having the structure C-9 is disclosed as being particularly effective as a CETP inhibitor.

Substituted tetrahydronaphthalene compounds useful as CETP inhibitors are described in PCT Patent Application No. WO 9914174. Specifically described in that disclosure as a useful CETP inhibitor is (8S)-3-cyclopentyl-1-(4-fluorophenyl)-2-[(S)-fluoro(4-trifluoromethylphenyl) methyl]-8-hydroxy-6-spirocclobutyl-5,6,7,8-tetrahydronaphthalene.

Some 4-heteroaryl-tetrahydroquinolines useful as CETP inhibitors are described in PCT Patent Application No. WO 9914215. For example, that disclosure describes 3-(4-trifluoromethylbenzoyl)-5,6,7,8-tetrahydroquinolin-5-one as a useful CETP inhibitor.

Some combination therapies for the treatment of cardiovascular disease have been described in the literature. Combinations of IBAT inhibitors with HMG CoA reductase inhibitors useful for the treatment of cardiovascular disease are disclosed in U.S. patent application No. 09/037,308.

A combination therapy of fluvastatin and niceritrol is described by J. Sasaki et al. (Id.). Those researchers conclude that the combination of fluvastatin with niceritrol "at a dose of 750 mg/day dose does not appear to augment or attenuate beneficial effects of fluvastatin."

L. Cashin-Hemphill et al. (J. Am. Med. Assoc., 264 (23), 3013–17 (1990)) describe beneficial effects of a combination therapy of colestipol and niacin on coronary atherosclerosis. The described effects include nonprogression and regression in native coronary artery lesions.

A combination therapy of acipimox and simvastatin shows beneficial HDL effects in patients having high triglyceride levels (N. Hoogerbrugge et al., J. Internal Med., 241, 151–55 (1997)).

Sitostanol ester margarine and pravastatin combination therapy is described by H. Gylling et al. (J. Lipid Res., 37, 1776–85 (1996)). That therapy is reported to simultaneously inhibit cholesterol absorption and lower LDL cholesterol significantly in non-insulin-dependent diabetic men.

Brown et al. (New Eng. J. Med., 323 (19), 1289–1339 (1990)) describe a combination therapy of lovastatin and colestipol which reduces atherosclerotic lesion progress on and increase lesion regression relative to lovastatin alone.

A combination therapy of an apoB secretion inhibitor with a CETP inhibitor was disclosed by Chang et al. in PCT Patent Application No. WO 9823593.

Buch et al. (PCT Patent Application No. WO 9911263) describe a combination therapy comprising amlodipine and a statin compound for treating subjects suffering from angina pectoris, atherosclerosis, combined hypertension and hyperlipidemia, and to treat symptoms of cardiac arrest. Buch et al. describe in PCT Patent Application No. WO 9911259 a combination therapy comprising amlodipine and atorvastatin.

Scott et al. (PCT Patent Application No. WO 9911260) describe a combination therapy comprising atorvastatin and an antihypertensive agent.

Dettmar and Gibson (UK Patent Application No. GB 2329334 A) claim a therapeutic composition useful for reducing plasma low density lipoprotein and cholesterol levels, wherein the composition comprises an HMG CoA reductase inhibitor and a bile complexing agent.

The above references show continuing need to find safe, effective agents for the prophylaxis or treatment of cardiovascular diseases.

SUMMARY OF THE INVENTION

To address the continuing need to find safe and effective agents for the prophylaxis and treatment of cardiovascular diseases, combination therapies of cardiovascular drugs are now reported.

Among its several embodiments, the present invention provides a combination therapy comprising the use of a first amount of an IBAT inhibitor and a second amount of another cardiovascular therapeutic useful in the prophylaxis or treatment of hyperlipidemia, atherosclerosis, or hypercholesterolemia, wherein said first and second amounts together comprise an anti-hyperlipidemic condition effective amount, an anti-atherosclerotic condition effective amount, or an anti-hypercholesterolemic condition effective amount of the compounds. For example one of the many embodiments of the present invention is a combination therapy comprising therapeutic dosages of an IBAT inhibitor and a CETP inhibitor. A preferred embodiment of the present invention is a combination therapy comprising therapeutic dosages of a benzothiepine IBAT inhibitor and a CETP inhibitor.

A further embodiment of the instant invention comprises the use of any of the cardiovascular combination therapies described herein for the prophylaxis or treatment of hypercholesterolemia, atherosclerosis, or hyperlipidemia. Therefore, in one embodiment the present invention provides a method for the prophylaxis or treatment of a hyperlipidemic condition comprising administering to a patient in need thereof a combination in unit dosage form wherein the combination comprises a first amount of an ileal bile acid transport inhibiting compound and a second amount of a CETP inhibiting compound wherein the first amount and the second amount together comprise an anti-hyperlipidemic condition effective amount of the compounds.

In another embodiment, the present invention provides a method for the prophylaxis or treatment of an atherosclerotic condition comprising administering to a patient in need thereof a combination in unit dosage form wherein the combination comprises a first amount of an ileal bile acid transport inhibiting compound and a second amount of a CETP inhibiting compound wherein the first amount and the second amount together comprise an anti-atherosclerotic condition effective amount of the compounds.

In still another embodiment, the present invention provides method for the prophylaxis or treatment of hypercholesterolemia comprising administering to a patient in need thereof a combination in unit dosage form wherein the combination comprises a first amount of an ileal bile acid transport inhibiting compound and a second amount of a CETP inhibiting compound wherein the first amount and the second amount together comprise an anti-hypercholesterolemic condition effective amount of the compounds.

Further scope of the applicability of the present invention will become apparent from the detailed description provided below. However, it should be understood that the following detailed description and examples, while indicating preferred embodiments of the invention, are given by way of illustration only since various changes and modifications within the spirit and scope of the invention will become apparent to those skilled in the art from this detailed description.

DETAILED DESCRIPTION OF THE PREFERRED EMBODIMENTS

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

a. Definitions

The following definitions are provided in order to aid the reader in understanding the detailed description of the present invention:

"Ileal bile acid transporter" or "IBAT" is synonymous with apical sodium co-dependent bile acid transporter, or ASBT.

"Benzothiepine IBAT inhibitor" means an ileal bile acid transport inhibitor which comprises a therapeutic compound comprising a 2,3,4,5-tetrahydro-1-benzothiepine 1,1-dioxde structure.

As used herein the term "CETP inhibitor" or "CETP inhibiting compound" means any therapeutic compound derived from chemical or biological sources which inhibits cholesteryl ester transfer protein activity.

"Combination therapy" means the administration of two or more therapeutic agents to treat a hyperlipidemic condition, for example atherosclerosis and hypercholesterolemia. Such administration encompasses co-administration of these therapeutic agents in a substantially simultaneous manner, such as in a single dosage form having a fixed ratio of active ingredients or in multiple, separate dosage forms for each inhibitor agent. In addition, such administration also encompasses use of each type of therapeutic agent in a sequential manner. In either case, the treatment regimen will provide beneficial effects of the drug combination in treating the hyperlipidemic condition.

The phrase "therapeutically effective" is intended to qualify the combined amount of inhibitors in the combination therapy. This combined amount will achieve the goal of reducing or eliminating the hyperlipidemic condition.

"Therapeutic compound" means a compound useful in the prophylaxis or treatment of a hyperlipidemic condition, including atherosclerosis and hypercholesterolemia.

b. Combinations

The combinations of the present invention will have a number of uses. For example, through dosage adjustment and medical monitoring, the individual dosages of the therapeutic compounds used in the combinations of the present invention will be lower than are typical for dosages of the therapeutic compounds when used in monotherapy. The dosage lowering will provide advantages including reduction of side effects of the individual therapeutic compounds when compared to the monotherapy. In addition, fewer side effects of the combination therapy compared with the monotherapies will lead to greater patient compliance with therapy regimens.

Another use of the present invention will be in combinations having complementary effects or complementary modes of action. For example, IBAT inhibitors control blood serum cholesterol levels by inhibiting the reabsorption of bile acids in the ileum. In contrast, CETP inhibitors inhibit the movement of cholesteryl esters and triglycerides between the various lipoproteins in the blood.

Compounds useful in the present invention encompass a wide range of therapeutic compounds. Some IBAT inhibitors useful in the present invention are disclosed in patent application no. PCT/US95/10863, herein incorporated by reference. More IBAT inhibitors are described in PCT/US97/04076, herein incorporated by reference. Still further IBAT inhibitors useful in the present invention are described in U.S. application Ser. No. 08/816,065, herein incorporated by reference. More IBAT inhibitor compounds useful in the present invention are described in WO 98/40375, herein incorporated by reference. Additional IBAT inhibitor compounds useful in the present invention are described in U.S. application Ser. No. 08/816,065, herein incorporated by reference. Further IBAT inhibiting compounds useful in the present invention are disclosed in U.S. Pat. No. 5,994,391, herein incorporated by reference. IBAT inhibitors of particular interest in the present invention include those shown in Table 1, as well as the diastereomers, enantiomers, racemates, salts, and tautomers of the IBAT inhibitors of Table 1.

TABLE 1

| Compound Number | Structure |
|---|---|
| B-1 | 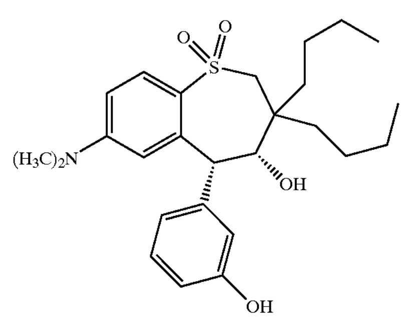 |

TABLE 1-continued
| Compound Number | Structure |
|---|---|
| B-2 | 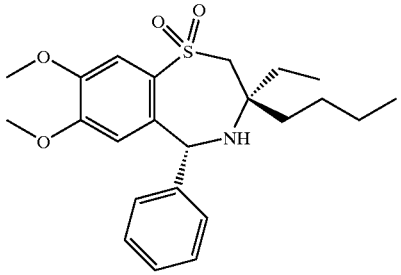<br>(3R,5R)-3-butyl-3-ethyl-2,3,4,5-tetrahydro-7,8-dimethoxy-5-phenyl-1-4-benzothiazepine 1,1-dioxide |
| B-3 | 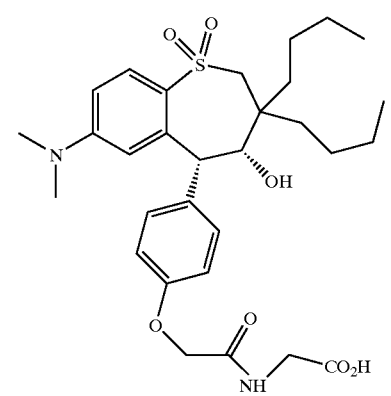 |
| B-4 | 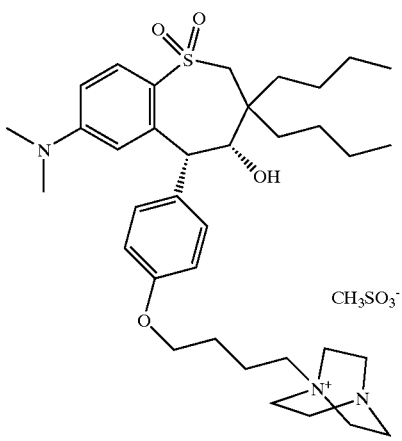 |
| B-5 | 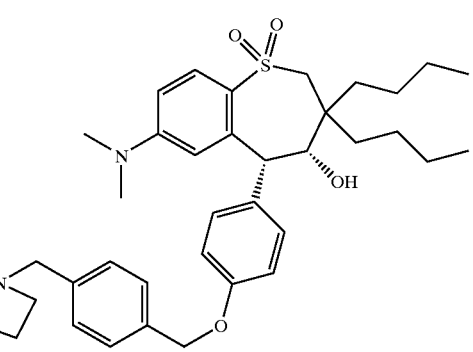 |

TABLE 1-continued

| Compound Number | Structure |
|---|---|
| B-6 | *(chemical structure)* |
| B-7 | *(chemical structure)* |
| B-8 | *(chemical structure)* |
| B-9 | *(chemical structure)* |

TABLE 1-continued
| Compound Number | Structure |
|---|---|
| B-10 | 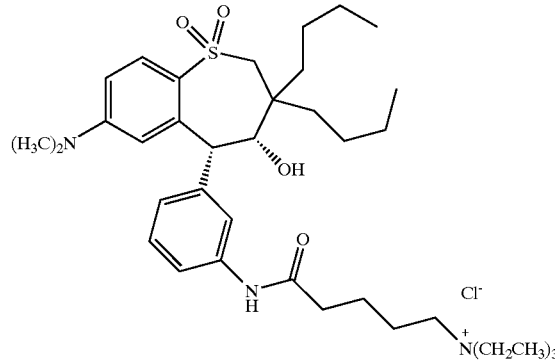 |
| B-11 | 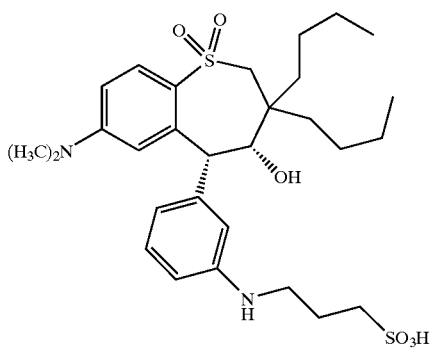 |
| B-12 | 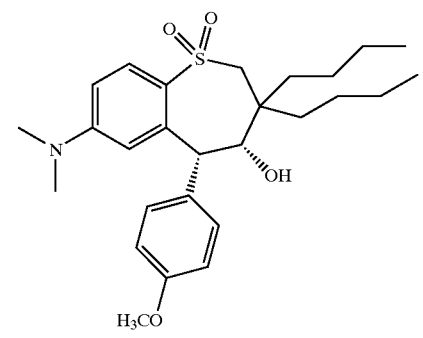 |
| B-13 | 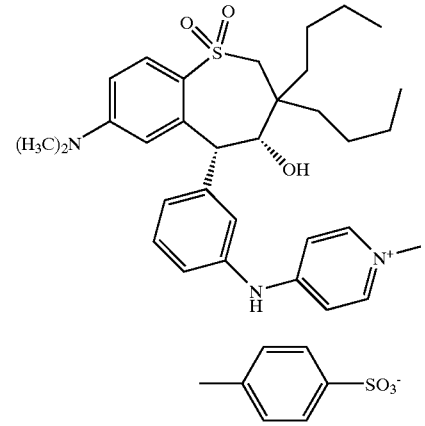 |

TABLE 1-continued
| Compound Number | Structure |
|---|---|
| B-14 | 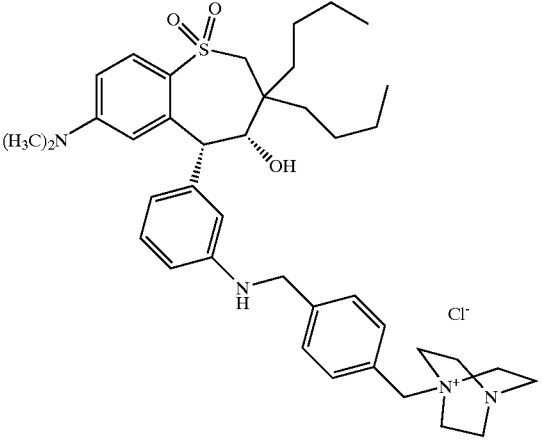 |
| B-15 | 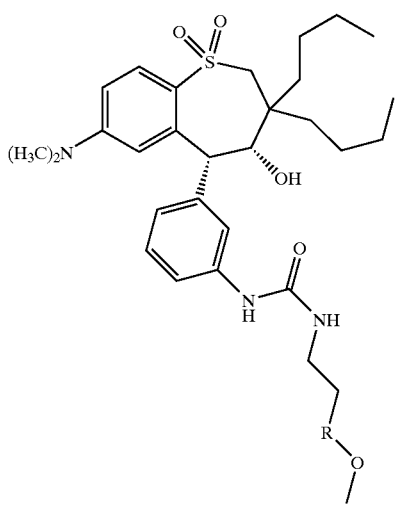
R = 5000 formual weight polyethyleneglycol |
| B-16 | 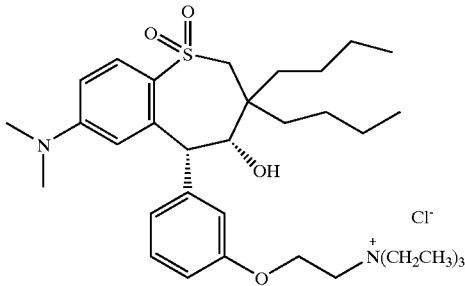 |

TABLE 1-continued

| Compound Number | Structure |
|---|---|
| B-17 | 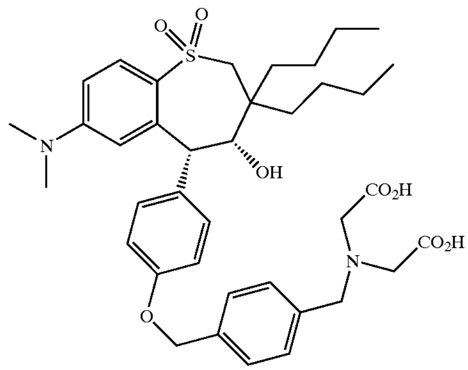 |
| B-18 | 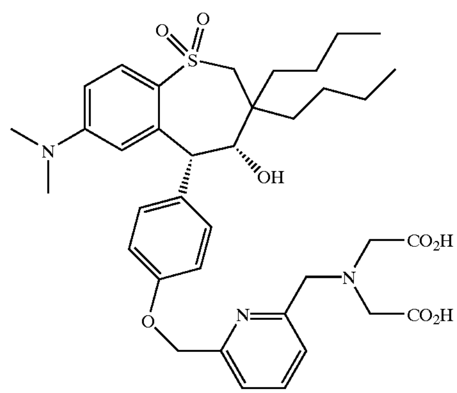 |
| B-19 | 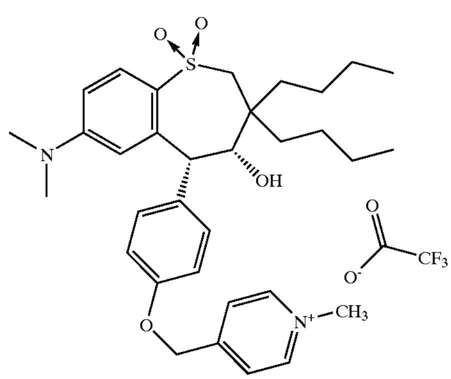 |
| B-20 | 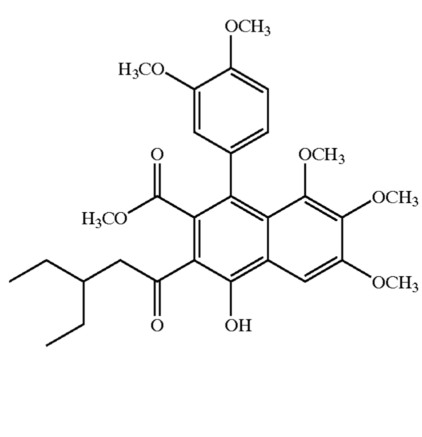 |

TABLE 1-continued

| Compound Number | Structure |
|---|---|
| B-21 | (structure) |
| B-22 | (structure) |
| B-23 | (structure) |
| B-24 | (structure) |

TABLE 1-continued

| Compound Number | Structure |
|---|---|
| B-25 | 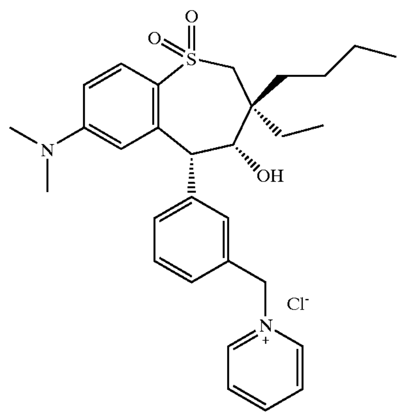 |
| B-26 | 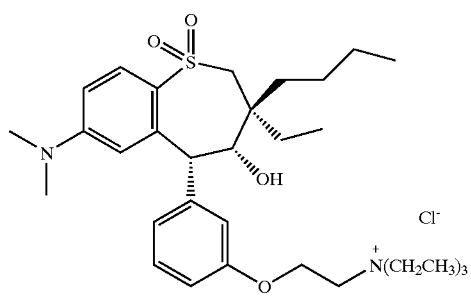 |
| B-27 | 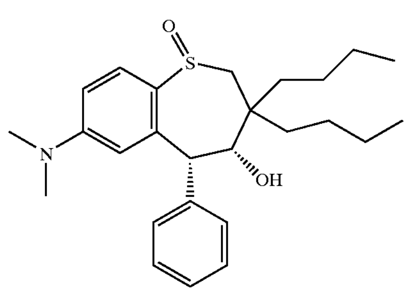 |

TABLE 1-continued
| Compound Number | Structure |
|---|---|
| B-28 | 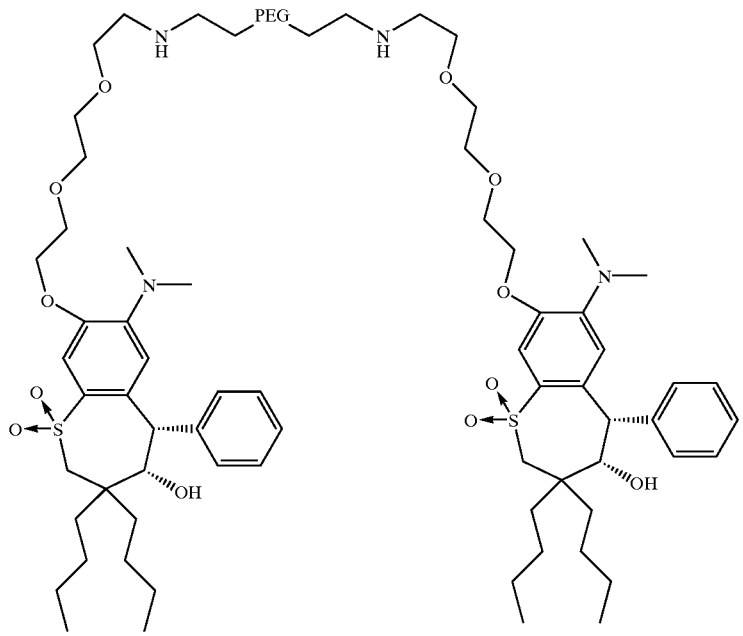<br>PEG = 3400 molecular weight polyethylene glycol polymer chain |
| B-29 | 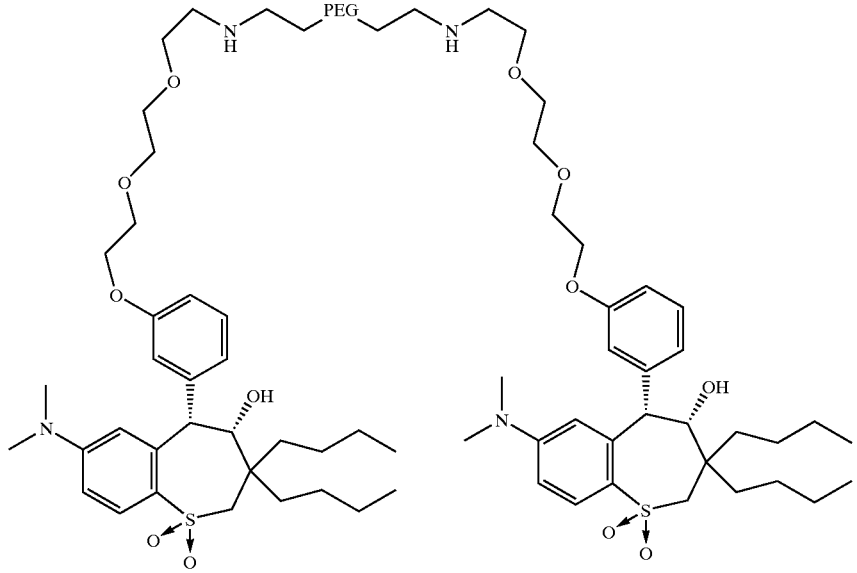<br>PEG = 3400 molecular weight polyethylene glycol polymer chain |

TABLE 1-continued
| Compound Number | Structure |
|---|---|
| B-30 | 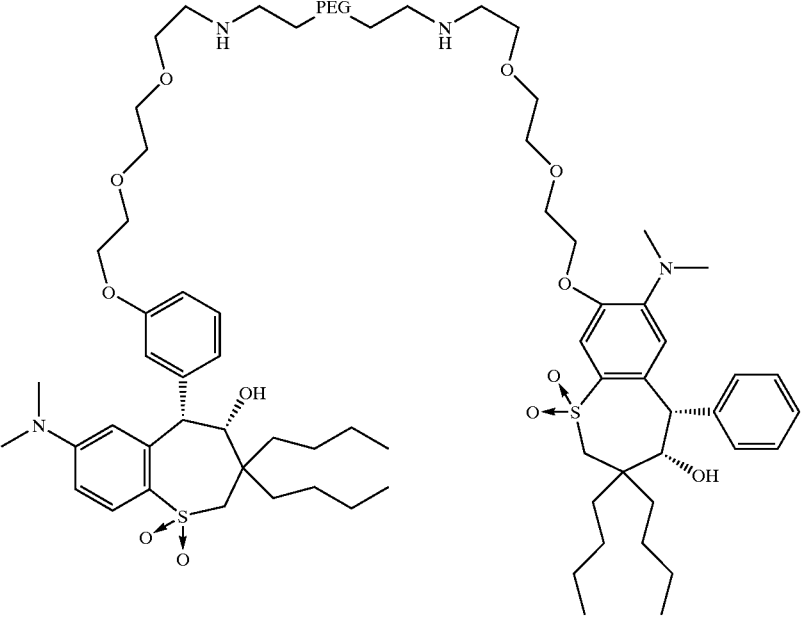 PEG = 3400 molecular weight polyethylene glycol polymer chain |
| B-31 | 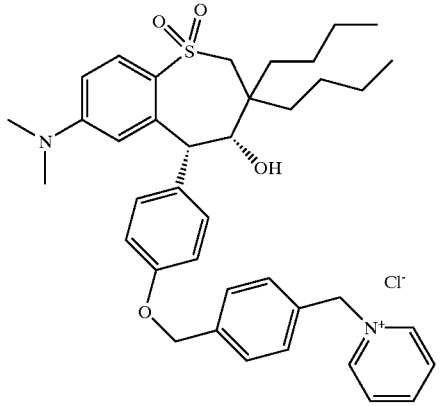 |
| B-32 | 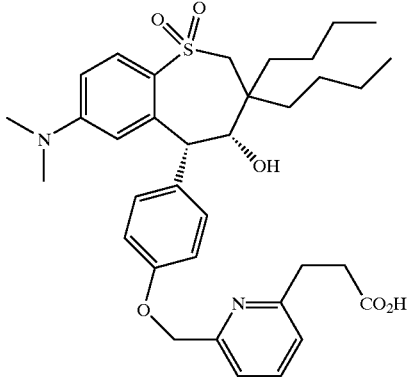 |

TABLE 1-continued
| Compound Number | Structure |
|---|---|
| B-33 | 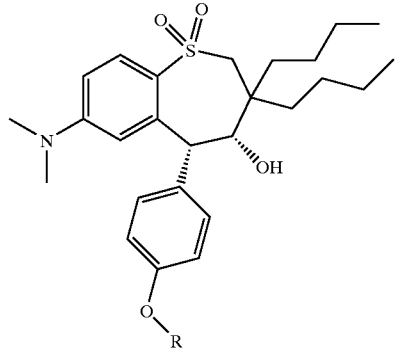<br>R = PEG 1000 |
| B-34 | 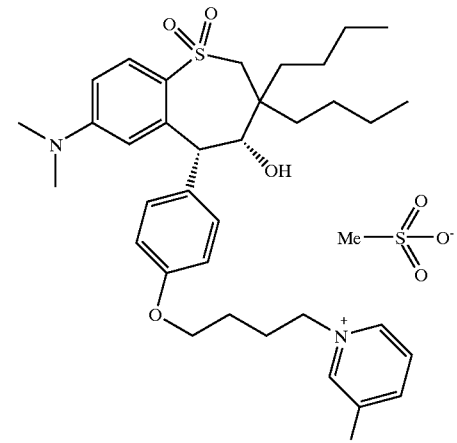 |
| B-35 | 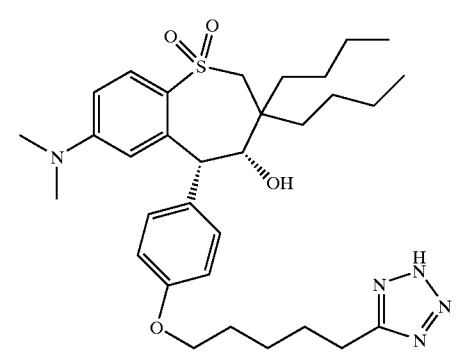 |

TABLE 1-continued
| Compound Number | Structure |
| --- | --- |
| B-36 | 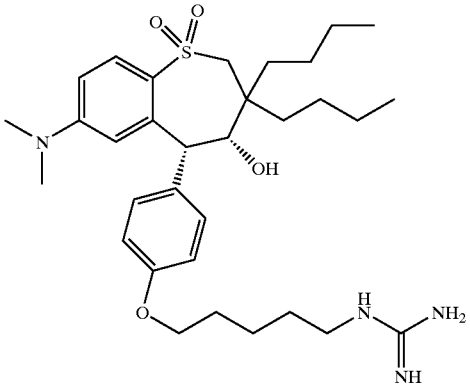 |
| B-37 | 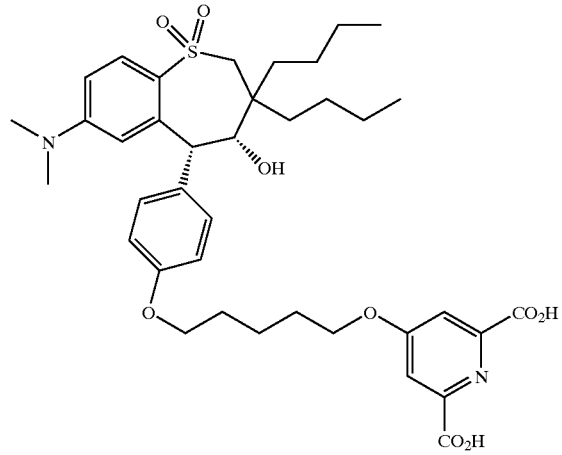 |
| B-38 | 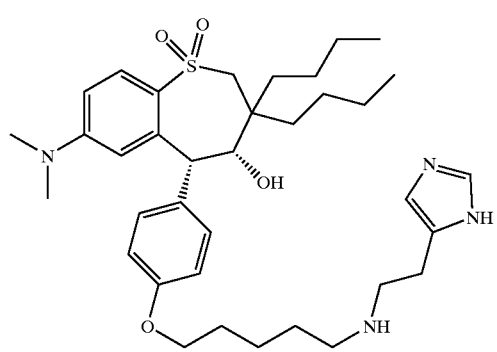 |

TABLE 1-continued

| Compound Number | Structure |
|---|---|
| B-39 | (structure shown) 2 Cl⁻ |

Some individual CETP inhibitor compounds useful in the present invention are separately described in the following individual patent applications, each of which is individually herein incorporated by reference.

R9. U.S. patent application Ser. No. 60/101661.
R10. U.S. patent application Ser. No. 60/101711.
R11. U.S. patent application Ser. No. 60/101660.
R12. U.S. patent application Ser. No. 60/101664.
R13. U.S. patent application Ser. No. 60/101668.
R14. U.S. patent application Ser. No. 60/101662.
R15. U.S. patent application Ser. No. 60/101663.
R16. U.S. patent application Ser. No. 60/101669.
R17. U.S. patent application Ser. No. 60/101667.
R18. U.S. patent application Ser. No. 09/401,916.
R19. U.S. patent application Ser. No. 09/405,524.
R20. U.S. patent application Ser. No. 09/404,638.
R21. U.S. patent application Ser. No. 09/404,638.
R22. U.S. patent application Ser. No. 09/400,915.
R23. U.S. Pat. No. 5,932,587.
R24. U.S. Pat. No. 5,925,645.

CETP inhibitor compounds of particular interest in the present invention include those shown in Table 2, as well as the diastereomers, enantiomers, racemates, salts, and tautomers of the CETP inhibitors of Table 2.

TABLE 2

| Compound Number | Structure |
|---|---|
| C-1 | (structure shown) |
| C-2 | (structure shown) |
| C-3 | (structure shown) |
| C-4 | (structure shown) |

TABLE 2-continued

| Compound Number | Structure |
|---|---|
| C-5 | 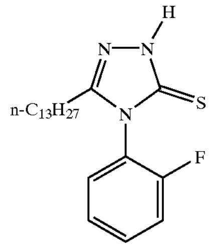 |
| C-6 | 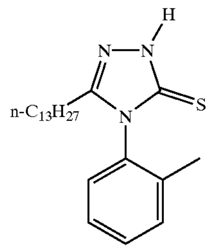 |
| C-7 | 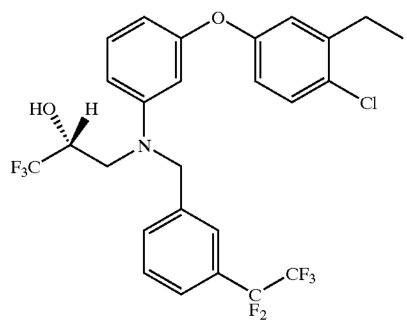 |
| C-8 | 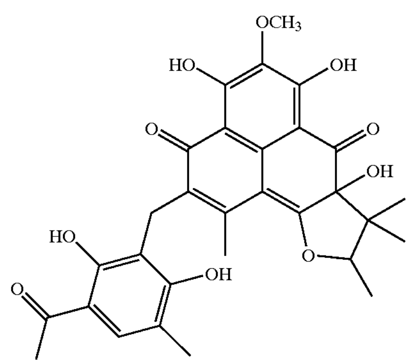 |
| C-9 | 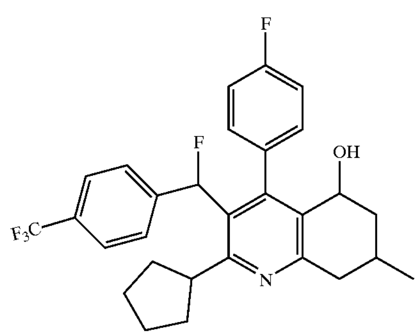 |
| C-10 | |
| C-11 | |
| C-12 | |
| C-13 | |

TABLE 2-continued

| Compound Number | Structure |
|---|---|
| C-14 | 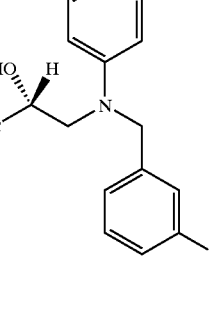 |
| C-15 | 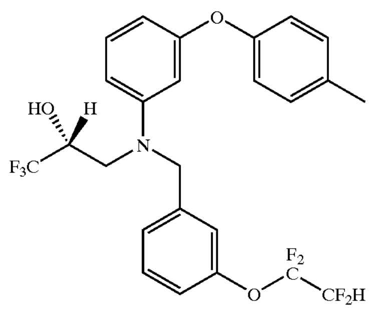 |
| C-16 | 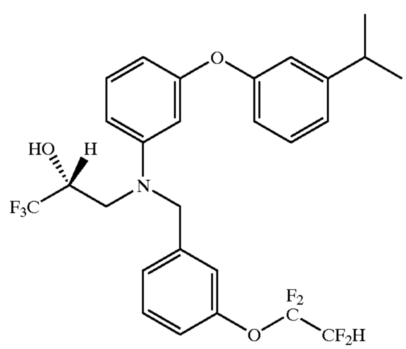 |
| C-17 | 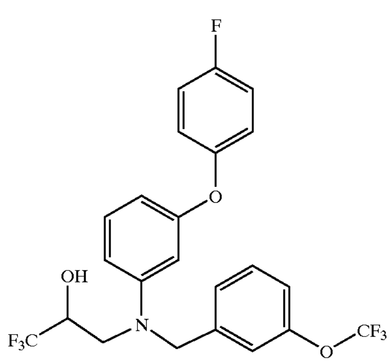 |

TABLE 2-continued

| Compound Number | Structure |
|---|---|
| C-18 | 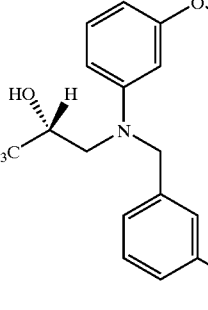 |
| C-19 | |
| C-20 | |

The compounds (for example, ileal bile acid transport inhibiting compounds or CETP inhibiting compounds) useful in the present invention can have no asymmetric carbon atoms, or, alternatively, the useful compounds can have one or more asymmetric carbon atoms. When the useful compound have one or more asymmetric carbon atoms, they therefore include racemates and stereoisomers, such as diastereomers and enantiomers, in both pure form and in admixture. Such stereoisomers can be prepared using conventional techniques, for example by reacting enantiomeric starting materials, or by separating isomers of compounds of the present invention.

Isomers may include geometric isomers, for example cis-isomers or trans-isomers across a double bond. All such isomers are contemplated among the compounds useful in the present invention.

The compounds useful in the present invention also include tautomers.

The compounds useful in the present invention as discussed below include their salts, solvates and prodrugs.

Dosages, Formulations, and Routes of Administration

The compositions of the present invention can be administered for the prophylaxis or treatment of hyperlipidemic diseases or conditions by any means, preferably oral, that produce contact of these compounds with their site of action in the body, for example in the ileum, the plasma, or the liver of a mammal, e.g., a human.

For the prophylaxis or treatment of the conditions referred to above, the compounds useful in the compositions and methods of the present invention can be used as he compound per se. Pharmaceutically acceptable salts are particularly suitable for medical applications because of their greater aqueous solubility relative to the parent compound. Such salts must clearly have a pharmaceutically acceptable anion or cation. Suitable pharmaceutically acceptable acid addition salts of the compounds of the present invention when possible include those derived from inorganic acids, such as hydrochloric, hydrobromic, phosphoric, metaphosphoric, nitric, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, succinic, toluenesulfonic, tartaric, and trifluoroacetic acids. The chloride salt is particularly preferred for medical purposes. Suitable pharmaceutically acceptable base salts include ammonium salts, alkali metal salts such as sodium and potassium salts, and alkaline earth salts such as magnesium and calcium salts.

The anions useful in the present invention are, of course, also required to be pharmaceutically acceptable and are also selected from the above list.

The compounds useful in the present invention can be presented with an acceptable carrier in the form of a pharmaceutical composition. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmacologically active substances can also be present, including other compounds of the present invention. The pharmaceutical compositions of the invention can be prepared by any of the well known techniques of pharmacy, consisting essentially of admixing the components.

Optionally, the combination of the present invention can comprise a composition comprising an ileal bile acid transport inhibiting compound and a CETP inhibiting compound. In such a composition, the ileal bile acid transport inhibiting compound and the CETP inhibiting compound can be present in a single dosage form, for example a pill, a capsule, or a liquid which contains both of the compounds.

These compounds can be administered by any conventional means available for use in conjunction with pharmaceuticals, either as individual therapeutic compounds or as a combination of therapeutic compounds.

The amount of compound which is required to achieve the desired biological effect will, of course, depend on a number of factors such as the specific compound chosen, the use for which it is intended, the mode of administration, and the clinical condition of the recipient.

In general, a total daily dose of an IBAT inhibitor can be in the range of from about 0.01 to about 1000 mg/day, preferably from about 0.1 mg to about 50 mg/day, more preferably from about 1 to about 10 mg/day.

For a CETP inhibitor, a daily dose of about 0.01 to about 100 mg/kg body weight/day, and preferably between about 0.5 to about 20 mg/kg body weight/day, may generally be appropriate.

The daily doses described in the preceding paragraphs for the various therapeutic compounds can be administered to the patient in a single dose, or in proportionate multiple subdoses. Subdoses can be administered 2 to 6 times per day. Doses can be in sustained release form effective to obtain desired results.

In the case of pharmaceutically acceptable salts, the weights indicated above refer to the weight of the acid equivalent or the base equivalent of the therapeutic compound derived from the salt.

Oral delivery of the combinations of the present invention can include formulations, as are well known in the art, to provide prolonged or sustained delivery of the drug to the gastrointestinal tract by any number of mechanisms. These include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. For some of the therapeutic compounds useful in the present invention (e.g., IBAT inhibitors or CETP inhibitors), the intended effect is to extend the time period over which the active drug molecule is delivered to the site of action (e.g., the ileum) by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethylcellulose phthalate and anionic polymers of methacrylic acid and methacrylic acid methyl ester.

The combinations of the present invention can be delivered orally either in a solid, in a semi-solid, or in a liquid form. When in a liquid or in a semi-solid form, the combinations of the present invention can, for example, be in the form of a liquid, syrup, or contained in a gel capsule (e.g., a gel cap). In one embodiment, when an IBAT inhibitor is used in a combination of the present invention, the IBAT inhibitor can be provided in the form of a liquid, syrup, or contained in a gel capsule. In another embodiment, when a CETP inhibitor is used in a combination of the present invention, the CETP inhibitor can be provided in the form of a liquid, syrup, or contained in a gel capsule.

The dose of any of these therapeutic compounds can be conveniently administered as an infusion of from about 10 ng/kg body weight to about 100 ng/kg body weight per minute. Infusion fluids suitable for this purpose can contain, for example, from about 0.1 ng to about 10 mg, preferably from about 1 ng to about 10 mg per milliliter. Unit doses can contain, for example, from about 1 mg to about 10 g of the compound of the present invention. Thus, ampoules for injection can contain, for example, from about 1 mg to about 100 mg.

Pharmaceutical compositions according to the present invention include those suitable for oral, rectal, topical, buccal (e.g., sublingual), and parenteral (e.g., subcutaneous, intramuscular, intradermal, or intravenous) administration, although the most suitable route in any given case will depend on the nature and severity of the condition being treated and on the nature of the particular compound which is being used. In most cases, the preferred route of administration is oral.

Pharmaceutical compositions suitable for oral administration can be presented in discrete units, such as capsules, cachets, lozenges, or tablets, each containing a predetermined amount of at least one therapeutic compound useful in the present invention; as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active compound(s) and the carrier (which can constitute one or more accessory ingredients). In general, the compositions are prepared by uniformly and intimately admixing the active compound with a liquid or finely divided solid carrier, or both, and then, if necessary, shaping the product. For example, a table; can be prepared by compressing or molding a powder or granules of the compound, optionally with one or more assessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Molded tablets can be made by molding, in a suitable machine, the powdered compound moistened with an inert liquid diluent.

Pharmaceutical compositions suitable for buccal (sublingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration conveniently comprise sterile aqueous preparations of a compound of the present invention. These preparations are preferably administered intravenously, although administration can also be effected by means of subcutaneous, intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of a compound disclosed herein.

Pharmaceutical compositions suitable for rectal administration are preferably presented as unit-dose suppositories. These can be prepared by admixing a compound of the present invention with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which can be used include petroleum jelly (e.g., Vaseline), lanolin, polyethylene glycols, alcohols, and combinations of two or more thereof. The active compound is generally present at a concentration of from 0.1 to 50% w/w of the composition, for example, from 0.5 to 2%.

Transdermal administration is also possible. Pharmaceutical compositions suitable for transdermal administration can be presented as discrete patches adapted to remain in intimate contact with the epidermis of the recipient for a prolonged period of time. Such patches suitably contain a compound of the present invention in an optionally buffered, aqueous solution, dissolved and/or dispersed in an adhesive, or dispersed in a polymer. A suitable concentration of the active compound is about 1% to 35%, preferably about 3% to 15%. As one particular possibility, the compound can be delivered from the patch by electrotransport or iontophoresis, for example, as described in *Pharmaceutical Research,* 3(6), 318 (1986).

In any case, the amount of active ingredient that can be combined with carrier materials to produce a single dosage form to be administered will vary depending upon the host treated and the particular mode of administration.

The solid dosage forms for oral administration including capsules, tablets, pills, powders, gel caps, and granules noted above comprise one or more compounds useful in the present invention admixed with at least one inert diluent such as sucrose, lactose, or starch. Such dosage forms may also comprise, as in normal practice, additional substances other than inert diluents, e.g., lubricating agents such as magnesium stearate or solubilizing agents such as cyclodextrins. In the case of capsules, tablets, powders, granules, gel caps, and pills, the dosage forms may also comprise buffering agents. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Injectable preparations, for example, sterile injectable aqueous or oleaginous suspensions may be formulated according to the known art using suitable dispersing or setting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutically acceptable carriers encompass all the foregoing and the like.

In combination therapy, administration of two or more of the therapeutic agents useful in the present invention may take place sequentially in separate formulations, or may be accomplished by simultaneous administration in a single formulation or separate formulations. Administration may be accomplished by oral route, or by intravenous, intramuscular, or subcutaneous injections. The formulation may be in the form of a bolus, or in the form of aqueous or non-aqueous isotonic sterile injection solutions or suspensions. These solutions and suspensions may be prepared from sterile powders or granules having one or more pharmaceutically-acceptable carriers or diluents, or a binder such as gelatin or hydroxypropylmethyl cellulose, together with one or more of a lubricant, preservative, surface active or dispersing agent.

For oral administration, the pharmaceutical composition may be in the form of, for example, a tablet, capsule, suspension, or liquid. Capsules, tablets, etc., can be prepared by conventional methods well known in the art. The pharmaceutical composition is preferably made in the form of a dosage unit containing a particular amount of the active ingredient or ingredients. Examples of dosage units are tablets or capsules. These may with advantage contain one or more therapeutic compound in an amount described above. For example, in the case of an IBAT inhibitor, the dose range may be from about 0.01 mg/day to about 500 mg/day or any other dose, dependent upon the specific inhibitor, as is known in the art. In the case of an bile acid sequestrant the dose range can be from about 1,000 mg/day to about 30,000 mg/day or any other dose, dependent upon the specific bile acid sequestrant, as is known in the art.

The active ingredients may also be administered by injection as a composition wherein, for example, saline, dextrose, or water may be used as a suitable carrier. A suitable daily dose of each active therapeutic compound is one that achieves the same blood serum level as produced by oral administration as described above.

The therapeutic compounds may further be administered by any combination of oral/oral, oral/parenteral, or parenteral/parenteral route.

Pharmaceutical compositions for use in the treatment methods of the present invention may be administered in oral form or by intravenous administration. Oral administration of the combination therapy is preferred. Dosing for oral administration may be with a regimen calling for single daily dose, or for a single dose every other day, or for multiple, spaced doses throughout the day. The therapeutic compounds which make up the combination therapy may be administered simultaneously, either in a combined dosage form or in separate dosage forms intended for substantially simultaneous oral administration. The therapeutic compounds which make up the combination therapy may also be administered sequentially, with either therapeutic compound being administered by a regimen calling for two-step ingestion. Thus, a regimen may call for sequential administration of the therapeutic compounds with spaced-apart ingestion of the separate, active agents. The time period between the multiple ingestion steps may range from a few minutes to several hours, depending upon the properties of each therapeutic compound such as potency, solubility, bioavailability, plasma half-life and kinetic profile of the therapeutic compound, as well as depending upon the effect of food ingestion and the age and condition of the patient. Circadian variation of the target molecule concentration may also determine the optimal dose interval. The therapeutic compounds of the combined therapy whether administered simultaneously, substantially simultaneously, or sequentially, may involve a regimen calling for administration of one therapeutic compound by oral route and another therapeutic compound by intravenous route. Whether the therapeutic compounds of the combined therapy are administered by oral or intravenous route, separately or together, each such therapeutic compound will be contained in a suitable pharmaceutical formulation of pharmaceutically-acceptable excipients, diluents or other formulations components. Examples of suitable pharmaceutically-acceptable formulations containing the therapeutic compounds for oral administration are given above.

Treatment Regimen

The dosage regimen to prevent, give relief from, or ameliorate a disease condition having hyperlipidemia as an element of the disease, e.g., atherosclerosis, or to protect against or treat further high cholesterol plasma or blood levels with the compounds and/or compositions of the present invention is selected in accordance with a variety of factors. These include the type, age, weight, sex, diet, and medical condition of the patient, the severity of the disease, the route of administration, pharmacological considerations such as the activity, efficacy, pharmacokinetics and toxicology profiles of the particular compound employed, whether a drug delivery system as utilized, and whether the compound is administered as part of a drug combination. Thus, the dosage regimen actually employed may vary widely and therefore deviate from the preferred dosage regimen set forth above.

Initial treatment of a patient suffering from a hyperlipidemic condition can begin with the dosages indicated above. Treatment should generally be continued as necessary over a period of several weeks to several months or years until the hyperlipidemic disease condition has been controlled or eliminated. Patients undergoing treatment with the compounds or compositions disclosed herein can be routinely monitored by, for example, measuring serum LDL and total cholesterol levels by any of the methods well known in the art, to determine the effectiveness of the combination therapy. Continuous analysis of such data permits modification of the treatment regimen during therapy so that optimal effective amounts of each type of therapeutic compound are administered at any point in time, and so that the duration of treatment can be determined as well. In this way, the treatment regimen/dosing schedule can be rationally modified over the course of therapy so that the lowest amount of the therapeutic compounds which together exhibit satisfactory effectiveness is administered, and so that administration is continued only so long as is necessary to successfully treat the hyperlipidemic condition.

A potential advantage of the combination therapy disclosed herein may be reduced dosage amount of of any individual therapeutic compound, or all therapeutic compounds, effective in treating hyperlipidemic conditions such as atherosclerosis and hypercholesterolemia. The dosage lowering will provide advantages including reduction of side effects of the individual therapeutic compounds when compared to the monotherapy.

One of the several embodiments of the present invention comprises a combination therapy comprising the use of a first amount of an IBAT inhibitor and a second amount of another cardiovascular therapeutic useful in the prophylaxis or treatment of hyperlipidemia, atherosclerosis, or hypercholesterolemia wherein said first and second amounts together comprise an anti-hyperlipidemic condition effective amount, an anti-atherosclerotic condition effective amount, or an anti-hypercholesterolemic condition effective amount of said compounds. For example one of the many embodiments of the present invention is a combination therapy comprising therapeutic dosages of an IBAT inhibitor and a CETP inhibitor. A preferred embodiment of the present invention is a combination therapy comprising therapeutic dosages of a benzothiepine IBAT inhibitor and a CETP inhibitor.

The embodiments of the present invention can comprise a combination therapy using two or more of the therapeutic compounds described or incorporated herein. The combination therapy can comprise two or more therapeutic compounds from different classes of chemistry, e.g., an IBAT inhibitor can be therapeutically combined with a CETP inhibitor. Therapeutic combinations can comprise more than two therapeutic compounds. For example, the therapy can comprise the use of an IBAT inhibitor, a CETP inhibitor, and a HMG CoA reductase inhibitor. Alternatively, two or more therapeutic compounds from the same class of chemistry can comprise the therapy, e.g. a combination therapy comprising two or more IBAT inhibitors or two or more CETP inhibitors.

A further embodiment of the instant invention comprises the use of any of the cardiovascular combination therapies described herein for the prophylaxis or treatment of hypercholesterolemia, atherosclerosis, or hyperlipidemia.

The following non-limiting examples serve to illustrate various aspects of the present invention.

Examples

Table 3 illustrates examples of some of the many combinations of the present invention wherein the combination comprises a first amount of IBAT inhibitor and a second amount of a CETP inhibitor, wherein said first and second amounts together comprise an anti-hyperlipidemic condition effective amount, an anti-atherosclerotic condition effective amount, or an anti-hypercholesterolemic condition effective amount of said compounds.

TABLE 3

| Example Number | Component 1 | Component 2 |
|---|---|---|
| 1 | B-1 | C-1 |
| 2 | B-1 | C-2 |
| 3 | B-1 | C-3 |
| 4 | B-1 | C-4 |
| 5 | B-1 | C-5 |
| 6 | B-1 | C-6 |
| 7 | B-1 | C-7 |
| 8 | B-1 | C-8 |
| 9 | B-1 | C-9 |
| 10 | B-1 | C-10 |

TABLE 3-continued

| Example Number | Component 1 | Component 2 |
| --- | --- | --- |
| 11 | B-1 | C-11 |
| 12 | B-1 | C-12 |
| 13 | B-1 | C-13 |
| 14 | B-1 | C-14 |
| 15 | B-1 | C-15 |
| 16 | B-1 | C-16 |
| 17 | B-1 | C-17 |
| 18 | B-1 | C-18 |
| 19 | B-1 | C-19 |
| 20 | B-1 | C-20 |
| 21 | B-2 | C-1 |
| 22 | B-2 | C-2 |
| 23 | B-2 | C-3 |
| 24 | B-2 | C-4 |
| 25 | B-2 | C-5 |
| 26 | B-2 | C-6 |
| 27 | B-2 | C-7 |
| 28 | B-2 | C-8 |
| 29 | B-2 | C-9 |
| 30 | B-2 | C-10 |
| 31 | B-2 | C-11 |
| 32 | B-2 | C-12 |
| 33 | B-2 | C-13 |
| 34 | B-2 | C-14 |
| 35 | B-2 | C-15 |
| 36 | B-2 | C-16 |
| 37 | B-2 | C-17 |
| 38 | B-2 | C-18 |
| 39 | B-2 | C-19 |
| 40 | B-2 | C-20 |
| 41 | B-3 | C-1 |
| 42 | B-3 | C-2 |
| 43 | B-3 | C-3 |
| 44 | B-3 | C-4 |
| 45 | B-3 | C-5 |
| 46 | B-3 | C-6 |
| 47 | B-3 | C-7 |
| 48 | B-3 | C-8 |
| 49 | B-3 | C-9 |
| 50 | B-3 | C-10 |
| 51 | B-3 | C-11 |
| 52 | B-3 | C-12 |
| 53 | B-3 | C-13 |
| 54 | B-3 | C-14 |
| 55 | B-3 | C-15 |
| 56 | B-3 | C-16 |
| 57 | B-3 | C-17 |
| 58 | B-3 | C-18 |
| 59 | B-3 | C-19 |
| 60 | B-3 | C-20 |
| 61 | B-4 | C-1 |
| 62 | B-4 | C-2 |
| 63 | B-4 | C-3 |
| 64 | B-4 | C-4 |
| 65 | B-4 | C-5 |
| 66 | B-4 | C-6 |
| 67 | B-4 | C-7 |
| 68 | B-4 | C-8 |
| 69 | B-4 | C-9 |
| 70 | B-4 | C-10 |
| 71 | B-4 | C-11 |
| 72 | B-4 | C-12 |
| 73 | B-4 | C-13 |
| 74 | B-4 | C-14 |
| 75 | B-4 | C-15 |
| 76 | B-4 | C-16 |
| 77 | B-4 | C-17 |
| 78 | B-4 | C-18 |
| 79 | B-4 | C-19 |
| 80 | B-4 | C-20 |
| 81 | B-5 | C-1 |
| 82 | B-5 | C-2 |
| 83 | B-5 | C-3 |
| 84 | B-5 | C-4 |
| 85 | B-5 | C-5 |
| 86 | B-5 | C-6 |
| 87 | B-5 | C-7 |
| 88 | B-5 | C-8 |
| 89 | B-5 | C-9 |
| 90 | B-5 | C-10 |
| 91 | B-5 | C-11 |
| 92 | B-5 | C-12 |
| 93 | B-5 | C-13 |
| 94 | B-5 | C-14 |
| 95 | B-5 | C-15 |
| 96 | B-5 | C-16 |
| 97 | B-5 | C-17 |
| 98 | B-5 | C-18 |
| 99 | B-5 | C-19 |
| 100 | B-5 | C-20 |
| 101 | B-6 | C-1 |
| 102 | B-6 | C-2 |
| 103 | B-6 | C-3 |
| 104 | B-6 | C-4 |
| 105 | B-6 | C-5 |
| 106 | B-6 | C-6 |
| 107 | B-6 | C-7 |
| 108 | B-6 | C-8 |
| 109 | B-6 | C-9 |
| 110 | B-6 | C-10 |
| 111 | B-6 | C-11 |
| 112 | B-6 | C-12 |
| 113 | B-6 | C-13 |
| 114 | B-6 | C-14 |
| 115 | B-6 | C-15 |
| 116 | B-6 | C-16 |
| 117 | B-6 | C-17 |
| 118 | B-6 | C-18 |
| 119 | B-6 | C-19 |
| 120 | B-6 | C-20 |
| 121 | B-7 | C-1 |
| 122 | B-7 | C-2 |
| 123 | B-7 | C-3 |
| 124 | B-7 | C-4 |
| 125 | B-7 | C-5 |
| 126 | B-7 | C-6 |
| 127 | B-7 | C-7 |
| 128 | B-7 | C-8 |
| 129 | B-7 | C-9 |
| 130 | B-7 | C-10 |
| 131 | B-7 | C-11 |
| 132 | B-7 | C-12 |
| 133 | B-7 | C-13 |
| 134 | B-7 | C-14 |
| 135 | B-7 | C-15 |
| 136 | B-7 | C-16 |
| 137 | B-7 | C-17 |
| 138 | B-7 | C-18 |
| 139 | B-7 | C-19 |
| 140 | B-7 | C-20 |
| 141 | B-8 | C-1 |
| 142 | B-8 | C-2 |
| 143 | B-8 | C-3 |
| 144 | B-8 | C-4 |
| 145 | B-8 | C-5 |
| 146 | B-8 | C-6 |
| 147 | B-8 | C-7 |
| 148 | B-8 | C-8 |
| 149 | B-8 | C-9 |
| 150 | B-8 | C-10 |
| 151 | B-8 | C-11 |
| 152 | B-8 | C-12 |
| 153 | B-8 | C-13 |
| 154 | B-8 | C-14 |
| 155 | B-8 | C-15 |
| 156 | B-8 | C-16 |
| 157 | B-8 | C-17 |
| 158 | B-8 | C-18 |
| 159 | B-8 | C-19 |
| 160 | B-8 | C-20 |
| 161 | B-9 | C-1 |
| 162 | B-9 | C-2 |

TABLE 3-continued

| Example Number | Component 1 | Component 2 |
|---|---|---|
| 163 | B-9 | C-3 |
| 164 | B-9 | C-4 |
| 165 | B-9 | C-5 |
| 166 | B-9 | C-6 |
| 167 | B-9 | C-7 |
| 168 | B-9 | C-8 |
| 169 | B-9 | C-9 |
| 170 | B-9 | C-10 |
| 171 | B-9 | C-11 |
| 172 | B-9 | C-12 |
| 173 | B-9 | C-13 |
| 174 | B-9 | C-14 |
| 175 | B-9 | C-15 |
| 176 | B-9 | C-16 |
| 177 | B-9 | C-17 |
| 178 | B-9 | C-18 |
| 179 | B-9 | C-19 |
| 180 | B-9 | C-20 |
| 181 | B-10 | C-1 |
| 182 | B-10 | C-2 |
| 183 | B-10 | C-3 |
| 184 | B-10 | C-4 |
| 185 | B-10 | C-5 |
| 186 | B-10 | C-6 |
| 187 | B-10 | C-7 |
| 188 | B-10 | C-8 |
| 189 | B-10 | C-9 |
| 190 | B-10 | C-10 |
| 191 | B-10 | C-11 |
| 192 | B-10 | C-12 |
| 193 | B-10 | C-13 |
| 194 | B-10 | C-14 |
| 195 | B-10 | C-15 |
| 196 | B-10 | C-16 |
| 197 | B-10 | C-17 |
| 198 | B-10 | C-18 |
| 199 | B-10 | C-19 |
| 200 | B-10 | C-20 |
| 201 | B-11 | C-1 |
| 202 | B-11 | C-2 |
| 203 | B-11 | C-3 |
| 204 | B-11 | C-4 |
| 205 | B-11 | C-5 |
| 206 | B-11 | C-6 |
| 207 | B-11 | C-7 |
| 208 | B-11 | C-8 |
| 209 | B-11 | C-9 |
| 210 | B-11 | C-10 |
| 211 | B-11 | C-11 |
| 212 | B-11 | C-12 |
| 213 | B-11 | C-13 |
| 214 | B-11 | C-14 |
| 215 | B-11 | C-15 |
| 216 | B-11 | C-16 |
| 217 | B-11 | C-17 |
| 218 | B-11 | C-18 |
| 219 | B-11 | C-19 |
| 220 | B-11 | C-20 |
| 221 | B-12 | C-1 |
| 222 | B-12 | C-2 |
| 223 | B-12 | C-3 |
| 224 | B-12 | C-4 |
| 225 | B-12 | C-5 |
| 226 | B-12 | C-6 |
| 227 | B-12 | C-7 |
| 228 | B-12 | C-8 |
| 229 | B-12 | C-9 |
| 230 | B-12 | C-10 |
| 231 | B-12 | C-11 |
| 232 | B-12 | C-12 |
| 233 | B-12 | C-13 |
| 234 | B-12 | C-14 |
| 235 | B-12 | C-15 |
| 236 | B-12 | C-16 |
| 237 | B-12 | C-17 |
| 238 | B-12 | C-18 |
| 239 | B-12 | C-19 |
| 240 | B-12 | C-20 |
| 241 | B-13 | C-1 |
| 242 | B-13 | C-2 |
| 243 | B-13 | C-3 |
| 244 | B-13 | C-4 |
| 245 | B-13 | C-5 |
| 246 | B-13 | C-6 |
| 247 | B-13 | C-7 |
| 248 | B-13 | C-8 |
| 249 | B-13 | C-9 |
| 250 | B-13 | C-10 |
| 251 | B-13 | C-11 |
| 252 | B-13 | C-12 |
| 253 | B-13 | C-13 |
| 254 | B-13 | C-14 |
| 255 | B-13 | C-15 |
| 256 | B-13 | C-16 |
| 257 | B-13 | C-17 |
| 258 | B-13 | C-18 |
| 259 | B-13 | C-19 |
| 260 | B-13 | C-20 |
| 261 | B-14 | C-1 |
| 262 | B-14 | C-2 |
| 263 | B-14 | C-3 |
| 264 | B-14 | C-4 |
| 265 | B-14 | C-5 |
| 266 | B-14 | C-6 |
| 267 | B-14 | C-7 |
| 268 | B-14 | C-8 |
| 269 | B-14 | C-9 |
| 270 | B-14 | C-10 |
| 271 | B-14 | C-11 |
| 272 | B-14 | C-12 |
| 273 | B-14 | C-13 |
| 274 | B-14 | C-14 |
| 275 | B-14 | C-15 |
| 276 | B-14 | C-16 |
| 277 | B-14 | C-17 |
| 278 | B-14 | C-18 |
| 279 | B-14 | C-19 |
| 280 | B-14 | C-20 |
| 281 | B-15 | C-1 |
| 282 | B-15 | C-2 |
| 283 | B-15 | C-3 |
| 284 | B-15 | C-4 |
| 285 | B-15 | C-5 |
| 286 | B-15 | C-6 |
| 287 | B-15 | C-7 |
| 288 | B-15 | C-8 |
| 289 | B-15 | C-9 |
| 290 | B-15 | C-10 |
| 291 | B-15 | C-11 |
| 292 | B-15 | C-12 |
| 293 | B-15 | C-13 |
| 294 | B-15 | C-14 |
| 295 | B-15 | C-15 |
| 296 | B-15 | C-16 |
| 297 | B-15 | C-17 |
| 298 | B-15 | C-18 |
| 299 | B-15 | C-19 |
| 300 | B-15 | C-20 |
| 301 | B-16 | C-1 |
| 302 | B-16 | C-2 |
| 303 | B-16 | C-3 |
| 304 | B-16 | C-4 |
| 305 | B-16 | C-5 |
| 306 | B-16 | C-6 |
| 307 | B-16 | C-7 |
| 308 | B-16 | C-8 |
| 309 | B-16 | C-9 |
| 310 | B-16 | C-10 |
| 311 | B-16 | C-11 |
| 312 | B-16 | C-12 |
| 313 | B-16 | C-13 |
| 314 | B-16 | C-14 |

TABLE 3-continued

| Example Number | Component 1 | Component 2 |
|---|---|---|
| 315 | B-16 | C-15 |
| 316 | B-16 | C-16 |
| 317 | B-16 | C-17 |
| 318 | B-16 | C-18 |
| 319 | B-16 | C-19 |
| 320 | B-16 | C-20 |
| 321 | B-17 | C-1 |
| 322 | B-17 | C-2 |
| 323 | B-17 | C-3 |
| 324 | B-17 | C-4 |
| 325 | B-17 | C-5 |
| 326 | B-17 | C-6 |
| 327 | B-17 | C-7 |
| 328 | B-17 | C-8 |
| 329 | B-17 | C-9 |
| 330 | B-17 | C-10 |
| 331 | B-17 | C-11 |
| 332 | B-17 | C-12 |
| 333 | B-17 | C-13 |
| 334 | B-17 | C-14 |
| 335 | B-17 | C-15 |
| 336 | B-17 | C-16 |
| 337 | B-17 | C-17 |
| 338 | B-17 | C-18 |
| 339 | B-17 | C-19 |
| 340 | B-17 | C-20 |
| 341 | B-18 | C-1 |
| 342 | B-18 | C-2 |
| 343 | B-18 | C-3 |
| 344 | B-18 | C-4 |
| 345 | B-18 | C-5 |
| 346 | B-18 | C-6 |
| 347 | B-18 | C-7 |
| 348 | B-18 | C-8 |
| 349 | B-18 | C-9 |
| 350 | B-18 | C-10 |
| 351 | B-18 | C-11 |
| 352 | B-18 | C-12 |
| 353 | B-18 | C-13 |
| 354 | B-18 | C-14 |
| 355 | B-18 | C-15 |
| 356 | B-18 | C-16 |
| 357 | B-18 | C-17 |
| 358 | B-18 | C-18 |
| 359 | B-18 | C-19 |
| 360 | B-18 | C-20 |
| 361 | B-19 | C-1 |
| 362 | B-19 | C-2 |
| 363 | B-19 | C-3 |
| 364 | B-19 | C-4 |
| 365 | B-19 | C-5 |
| 366 | B-19 | C-6 |
| 367 | B-19 | C-7 |
| 368 | B-19 | C-8 |
| 369 | B-19 | C-9 |
| 370 | B-19 | C-10 |
| 371 | B-19 | C-11 |
| 372 | B-19 | C-12 |
| 373 | B-19 | C-13 |
| 374 | B-19 | C-14 |
| 375 | B-19 | C-15 |
| 376 | B-19 | C-16 |
| 377 | B-19 | C-17 |
| 378 | B-19 | C-18 |
| 379 | B-19 | C-19 |
| 380 | B-19 | C-20 |
| 381 | B-20 | C-1 |
| 382 | B-20 | C-2 |
| 383 | B-20 | C-3 |
| 384 | B-20 | C-4 |
| 385 | B-20 | C-5 |
| 386 | B-20 | C-6 |
| 387 | B-20 | C-7 |
| 388 | B-20 | C-8 |
| 389 | B-20 | C-9 |
| 390 | B-20 | C-10 |
| 391 | B-20 | C-11 |
| 392 | B-20 | C-12 |
| 393 | B-20 | C-13 |
| 394 | B-20 | C-14 |
| 395 | B-20 | C-15 |
| 396 | B-20 | C-16 |
| 397 | B-20 | C-17 |
| 398 | B-20 | C-18 |
| 399 | B-20 | C-19 |
| 400 | B-20 | C-20 |
| 401 | B-21 | C-1 |
| 402 | B-21 | C-2 |
| 403 | B-21 | C-3 |
| 404 | B-21 | C-4 |
| 405 | B-21 | C-5 |
| 406 | B-21 | C-6 |
| 407 | B-21 | C-7 |
| 408 | B-21 | C-8 |
| 409 | B-21 | C-9 |
| 410 | B-21 | C-10 |
| 411 | B-21 | C-11 |
| 412 | B-21 | C-12 |
| 413 | B-21 | C-13 |
| 414 | B-21 | C-14 |
| 415 | B-21 | C-15 |
| 416 | B-21 | C-16 |
| 417 | B-21 | C-17 |
| 418 | B-21 | C-18 |
| 419 | B-21 | C-19 |
| 420 | B-21 | C-20 |
| 421 | B-22 | C-1 |
| 422 | B-22 | C-2 |
| 423 | B-22 | C-3 |
| 424 | B-22 | C-4 |
| 425 | B-22 | C-5 |
| 426 | B-22 | C-6 |
| 427 | B-22 | C-7 |
| 428 | B-22 | C-8 |
| 429 | B-22 | C-9 |
| 430 | B-22 | C-10 |
| 431 | B-22 | C-11 |
| 432 | B-22 | C-12 |
| 433 | B-22 | C-13 |
| 434 | B-22 | C-14 |
| 435 | B-22 | C-15 |
| 436 | B-22 | C-16 |
| 437 | B-22 | C-17 |
| 438 | B-22 | C-18 |
| 439 | B-22 | C-19 |
| 440 | B-22 | C-20 |
| 441 | B-23 | C-1 |
| 442 | B-23 | C-2 |
| 443 | B-23 | C-3 |
| 444 | B-23 | C-4 |
| 445 | B-23 | C-5 |
| 446 | B-23 | C-6 |
| 447 | B-23 | C-7 |
| 448 | B-23 | C-8 |
| 449 | B-23 | C-9 |
| 450 | B-23 | C-10 |
| 451 | B-23 | C-11 |
| 452 | B-23 | C-12 |
| 453 | B-23 | C-13 |
| 454 | B-23 | C-14 |
| 455 | B-23 | C-15 |
| 456 | B-23 | C-16 |
| 457 | B-23 | C-17 |
| 458 | B-23 | C-18 |
| 459 | B-23 | C-19 |
| 460 | B-23 | C-20 |
| 461 | B-24 | C-1 |
| 462 | B-24 | C-2 |
| 463 | B-24 | C-3 |
| 464 | B-24 | C-4 |
| 465 | B-24 | C-5 |
| 466 | B-24 | C-6 |

TABLE 3-continued

| Example Number | Component 1 | Component 2 |
| --- | --- | --- |
| 467 | B-24 | C-7 |
| 468 | B-24 | C-8 |
| 469 | B-24 | C-9 |
| 470 | B-24 | C-10 |
| 471 | B-24 | C-11 |
| 472 | B-24 | C-12 |
| 473 | B-24 | C-13 |
| 474 | B-24 | C-14 |
| 475 | B-24 | C-15 |
| 476 | B-24 | C-16 |
| 477 | B-24 | C-17 |
| 478 | B-24 | C-18 |
| 479 | B-24 | C-19 |
| 480 | B-24 | C-20 |
| 481 | B-25 | C-1 |
| 482 | B-25 | C-2 |
| 483 | B-25 | C-3 |
| 484 | B-25 | C-4 |
| 485 | B-25 | C-5 |
| 486 | B-25 | C-6 |
| 487 | B-25 | C-7 |
| 488 | B-25 | C-8 |
| 489 | B-25 | C-9 |
| 490 | B-25 | C-10 |
| 491 | B-25 | C-11 |
| 492 | B-25 | C-12 |
| 493 | B-25 | C-13 |
| 494 | B-25 | C-14 |
| 495 | B-25 | C-15 |
| 496 | B-25 | C-16 |
| 497 | B-25 | C-17 |
| 498 | B-25 | C-18 |
| 499 | B-25 | C-19 |
| 500 | B-25 | C-20 |
| 501 | B-26 | C-1 |
| 502 | B-26 | C-2 |
| 503 | B-26 | C-3 |
| 504 | B-26 | C-4 |
| 505 | B-26 | C-5 |
| 506 | B-26 | C-6 |
| 507 | B-26 | C-7 |
| 508 | B-26 | C-8 |
| 509 | B-26 | C-9 |
| 510 | B-26 | C-10 |
| 511 | B-26 | C-11 |
| 512 | B-26 | C-12 |
| 513 | B-26 | C-13 |
| 514 | B-26 | C-14 |
| 515 | B-26 | C-15 |
| 516 | B-26 | C-16 |
| 517 | B-26 | C-17 |
| 518 | B-26 | C-18 |
| 519 | B-26 | C-19 |
| 520 | B-26 | C-20 |
| 521 | B-27 | C-1 |
| 522 | B-27 | C-2 |
| 523 | B-27 | C-3 |
| 524 | B-27 | C-4 |
| 525 | B-27 | C-5 |
| 526 | B-27 | C-6 |
| 527 | B-27 | C-7 |
| 528 | B-27 | C-8 |
| 529 | B-27 | C-9 |
| 530 | B-27 | C-10 |
| 531 | B-27 | C-11 |
| 532 | B-27 | C-12 |
| 533 | B-27 | C-13 |
| 534 | B-27 | C-14 |
| 535 | B-27 | C-15 |
| 536 | B-27 | C-16 |
| 537 | B-27 | C-17 |
| 538 | B-27 | C-18 |
| 539 | B-27 | C-19 |
| 540 | B-27 | C-20 |
| 541 | B-28 | C-1 |
| 542 | B-28 | C-2 |
| 543 | B-28 | C-3 |
| 544 | B-28 | C-4 |
| 545 | B-28 | C-5 |
| 546 | B-28 | C-6 |
| 547 | B-28 | C-7 |
| 548 | B-28 | C-8 |
| 549 | B-28 | C-9 |
| 550 | B-28 | C-10 |
| 551 | B-28 | C-11 |
| 552 | B-28 | C-12 |
| 553 | B-28 | C-13 |
| 554 | B-28 | C-14 |
| 555 | B-28 | C-15 |
| 556 | B-28 | C-16 |
| 557 | B-28 | C-17 |
| 558 | B-28 | C-18 |
| 559 | B-28 | C-19 |
| 560 | B-28 | C-20 |
| 561 | B-29 | C-1 |
| 562 | B-29 | C-2 |
| 563 | B-29 | C-3 |
| 564 | B-29 | C-4 |
| 565 | B-29 | C-5 |
| 566 | B-29 | C-6 |
| 567 | B-29 | C-7 |
| 568 | B-29 | C-8 |
| 569 | B-29 | C-9 |
| 570 | B-29 | C-10 |
| 571 | B-29 | C-11 |
| 572 | B-29 | C-12 |
| 573 | B-29 | C-13 |
| 574 | B-29 | C-14 |
| 575 | B-29 | C-15 |
| 576 | B-29 | C-16 |
| 577 | B-29 | C-17 |
| 578 | B-29 | C-18 |
| 579 | B-29 | C-19 |
| 580 | B-29 | C-20 |
| 581 | B-30 | C-1 |
| 582 | B-30 | C-2 |
| 583 | B-30 | C-3 |
| 584 | B-30 | C-4 |
| 585 | B-30 | C-5 |
| 586 | B-30 | C-6 |
| 587 | B-30 | C-7 |
| 588 | B-30 | C-8 |
| 589 | B-30 | C-9 |
| 590 | B-30 | C-10 |
| 591 | B-30 | C-11 |
| 592 | B-30 | C-12 |
| 593 | B-30 | C-13 |
| 594 | B-30 | C-14 |
| 595 | B-30 | C-15 |
| 596 | B-30 | C-16 |
| 597 | B-30 | C-17 |
| 598 | B-30 | C-18 |
| 599 | B-30 | C-19 |
| 600 | B-30 | C-20 |
| 601 | B-31 | C-1 |
| 602 | B-31 | C-2 |
| 603 | B-31 | C-3 |
| 604 | B-31 | C-4 |
| 605 | B-31 | C-5 |
| 606 | B-31 | C-6 |
| 607 | B-31 | C-7 |
| 608 | B-31 | C-8 |
| 609 | B-31 | C-9 |
| 610 | B-31 | C-10 |
| 611 | B-31 | C-11 |
| 612 | B-31 | C-12 |
| 613 | B-31 | C-13 |
| 614 | B-31 | C-14 |
| 615 | B-31 | C-15 |
| 616 | B-31 | C-16 |
| 617 | B-31 | C-17 |
| 618 | B-31 | C-18 |

TABLE 3-continued

| Example Number | Component 1 | Component 2 |
|---|---|---|
| 619 | B-31 | C-19 |
| 620 | B-31 | C-20 |
| 621 | B-32 | C-1 |
| 622 | B-32 | C-2 |
| 623 | B-32 | C-3 |
| 624 | B-32 | C-4 |
| 625 | B-32 | C-5 |
| 626 | B-32 | C-6 |
| 627 | B-32 | C-7 |
| 628 | B-32 | C-8 |
| 629 | B-32 | C-9 |
| 630 | B-32 | C-10 |
| 631 | B-32 | C-11 |
| 632 | B-32 | C-12 |
| 633 | B-32 | C-13 |
| 634 | B-32 | C-14 |
| 635 | B-32 | C-15 |
| 636 | B-32 | C-16 |
| 637 | B-32 | C-17 |
| 638 | B-32 | C-18 |
| 639 | B-32 | C-19 |
| 640 | B-32 | C-20 |
| 641 | B-33 | C-1 |
| 642 | B-33 | C-2 |
| 643 | B-33 | C-3 |
| 644 | B-33 | C-4 |
| 645 | B-33 | C-5 |
| 646 | B-33 | C-6 |
| 647 | B-33 | C-7 |
| 648 | B-33 | C-8 |
| 649 | B-33 | C-9 |
| 650 | B-33 | C-10 |
| 651 | B-33 | C-11 |
| 652 | B-33 | C-12 |
| 653 | B-33 | C-13 |
| 654 | B-33 | C-14 |
| 655 | B-33 | C-15 |
| 656 | B-33 | C-16 |
| 657 | B-33 | C-17 |
| 658 | B-33 | C-18 |
| 659 | B-33 | C-19 |
| 660 | B-33 | C-20 |
| 661 | B-34 | C-1 |
| 662 | B-34 | C-2 |
| 663 | B-34 | C-3 |
| 664 | B-34 | C-4 |
| 665 | B-34 | C-5 |
| 666 | B-34 | C-6 |
| 667 | B-34 | C-7 |
| 668 | B-34 | C-8 |
| 669 | B-34 | C-9 |
| 670 | B-34 | C-10 |
| 671 | B-34 | C-11 |
| 672 | B-34 | C-12 |
| 673 | B-34 | C-13 |
| 674 | B-34 | C-14 |
| 675 | B-34 | C-15 |
| 676 | B-34 | C-16 |
| 677 | B-34 | C-17 |
| 678 | B-34 | C-18 |
| 679 | B-34 | C-19 |
| 680 | B-34 | C-20 |
| 681 | B-35 | C-1 |
| 682 | B-35 | C-2 |
| 683 | B-35 | C-3 |
| 684 | B-35 | C-4 |
| 685 | B-35 | C-5 |
| 686 | B-35 | C-6 |
| 687 | B-35 | C-7 |
| 688 | B-35 | C-8 |
| 689 | B-35 | C-9 |
| 690 | B-35 | C-10 |
| 691 | B-35 | C-11 |
| 692 | B-35 | C-12 |
| 693 | B-35 | C-13 |
| 694 | B-35 | C-14 |
| 695 | B-35 | C-15 |
| 696 | B-35 | C-16 |
| 697 | B-35 | C-17 |
| 698 | B-35 | C-18 |
| 699 | B-35 | C-19 |
| 700 | B-35 | C-20 |
| 701 | B-36 | C-1 |
| 702 | B-36 | C-2 |
| 703 | B-36 | C-3 |
| 704 | B-36 | C-4 |
| 705 | B-36 | C-5 |
| 706 | B-36 | C-6 |
| 707 | B-36 | C-7 |
| 708 | B-36 | C-8 |
| 709 | B-36 | C-9 |
| 710 | B-36 | C-10 |
| 711 | B-36 | C-11 |
| 712 | B-36 | C-12 |
| 713 | B-36 | C-13 |
| 714 | B-36 | C-14 |
| 715 | B-36 | C-15 |
| 716 | B-36 | C-16 |
| 717 | B-36 | C-17 |
| 718 | B-36 | C-18 |
| 719 | B-36 | C-19 |
| 720 | B-36 | C-20 |
| 721 | B-37 | C-1 |
| 722 | B-37 | C-2 |
| 723 | B-37 | C-3 |
| 724 | B-37 | C-4 |
| 725 | B-37 | C-5 |
| 726 | B-37 | C-6 |
| 727 | B-37 | C-7 |
| 728 | B-37 | C-8 |
| 729 | B-37 | C-9 |
| 730 | B-37 | C-10 |
| 731 | B-37 | C-11 |
| 732 | B-37 | C-12 |
| 733 | B-37 | C-13 |
| 734 | B-37 | C-14 |
| 735 | B-37 | C-15 |
| 736 | B-37 | C-16 |
| 737 | B-37 | C-17 |
| 738 | B-37 | C-18 |
| 739 | B-37 | C-19 |
| 740 | B-37 | C-20 |
| 741 | B-38 | C-1 |
| 742 | B-38 | C-2 |
| 743 | B-38 | C-3 |
| 744 | B-38 | C-4 |
| 745 | B-38 | C-5 |
| 746 | B-38 | C-6 |
| 747 | B-38 | C-7 |
| 748 | B-38 | C-8 |
| 749 | B-38 | C-9 |
| 750 | B-38 | C-10 |
| 751 | B-38 | C-11 |
| 752 | B-38 | C-12 |
| 753 | B-38 | C-13 |
| 754 | B-38 | C-14 |
| 755 | B-38 | C-15 |
| 756 | B-38 | C-16 |
| 757 | B-38 | C-17 |
| 758 | B-38 | C-18 |
| 759 | B-38 | C-19 |
| 760 | B-38 | C-20 |
| 761 | B-40 | C-1 |
| 762 | B-40 | C-2 |
| 763 | B-40 | C-3 |
| 764 | B-40 | C-4 |
| 765 | B-40 | C-5 |
| 766 | B-40 | C-6 |
| 767 | B-40 | C-7 |
| 768 | B-40 | C-8 |
| 769 | B-40 | C-9 |
| 770 | B-40 | C-10 |

TABLE 3-continued

| Example Number | Component 1 | Component 2 |
|---|---|---|
| 771 | B-40 | C-11 |
| 772 | B-40 | C-12 |
| 773 | B-40 | C-13 |
| 774 | B-40 | C-14 |
| 775 | B-40 | C-15 |
| 776 | B-40 | C-16 |
| 777 | B-40 | C-17 |
| 778 | B-40 | C-18 |
| 779 | B-40 | C-19 |
| 780 | B-40 | C-20 |

Biological Assays

The utility of the combinations of the present invention can be shown by the following assays. These assays are performed in vitro and in animal models essentially using procedures recognized to show the utility of the present invention.

In Vitro Assay of Compounds that Inhibit IBAT-mediated Uptake of [$^{14}$C]-Taurocholate (TC) in H14 Cells Baby hamster kidney cells (BHK) transfected with the cDNA of human IBAT (H14 cells) are seeded at 60,000 cells/well in 96 well Top-Count tissue culture plates for assays run within in 24 hours of seeding, 30,000 cells/well for assays run within 48 hours, and 10,000 cells/well for assays run within 72 hours.

On the day of assay, the cell monolayer is gently washed once with 100 μl assay buffer (Dulbecco's Modified Eagle's medium with 4.5 g/L glucose+0.2% (w/v) fatty acid free bovine serum albumin-(FAF)BSA). To each well 50 μl of a two-fold concentrate of test compound in assay buffer is added along with 50 μl of 6 μM [$^{14}$C]-taurocholate in assay buffer (final concentration of 3 μM [$^{14}$C]-taurocholate). The cell culture plates are incubated 2 hours at 37° C. prior to gently washing each well twice with 100 μl 4° C. Dulbecco's phosphate-buffered saline (PBS) containing 0.2% (w/v) (FAF)BSA. The wells are then gently washed once with 100 μl 4° C. PBS without (FAF)BSA. To each 200 μl of liquid scintillation counting fluid is added, the plates are heat sealed and shaken for 30 minutes at room temperature prior to measuring the amount of radioactivity in each well on a Packard Top-Count instrument.

In Vitro Assay of Compounds that Inhibit Uptake of [$^{14}$C]-Alanine

The alanine uptake assay is performed in an identical fashion to the taurocholate assay, with the exception that labeled alanine is substituted for the labeled taurocholate.

Measurement of Rat Fecal Bile Acid Concentration (FBA)

Total fecal output from individually housed rats is collected for 24 or 48 hours, dried under a stream of nitrogen, pulverized, mixed, and weighed. Approximately 0.1 gram is weighed out and extracted into an organic solvent (butanol/water). Following separation and drying, the residue is dissolved in methanol and the amount of bile acid present is measured enzymatically using the 3α-hydroxysteroid steroid dehydrogenase reaction with bile acids to reduce NAD. (see Mashige, F. et al. *Clin. Chem.*, 27, 1352 (1981), herein incorporated by reference).

Rat Gavage Assay

Male Wister rats (275–300 g) are to be administered IBAT inhibitors using an oral gavage procedure. Drug or vehicle 0.2% TWEEN 80 in water) is administered once a day (9:00–10:00 a.m.) for 4 days at varying dosages in a final volume of 2 mL per kilogram of body weight. (TWEEN 80 is a 20 molar polyethyleneoxide sorbitan monooleate surfactant manufactured by ICI Specialty Chemicals, Wilmington, Del. U.S.A.) Total fecal samples are collected during the final 48 hours of the treatment period and analyzed for bile acid content using an enzymatic assay as described below. Compound efficacy will be determined by comparison of the increase in fecal bile acid (FBA) concentration in treated rats to the mean FBA concentration of rats in the vehicle group.

[$^3$H]Taurocholate Uptake in Rabbit Brush Border Membrane Vesicles (BBMV)

Rabbit Ileal brush border membranes are to be prepared from frozen ileal mucosa by the calcium precipitation method describe by Malathi et al. (*Biochimica Biophysica Acta*, 554, 259 (1979), herein incorporated by reference). The method for measuring taurocholate is essentially as described by Kramer et al. (*Biochimica Biophysica Acta*, 1111, 93 (1992), herein incorporated by reference) except the assay volume will be 200 μl instead of 100 μl. Briefly, at room temperature a 190 μl solution containing 2 μM [$^3$H]-taurocholate(0.75 μCi), 20 mM tris, 100 mM NaCl, 100 mM mannitol pH 7.4 is incubated for 5 sec with 10 μl of brush border membrane vesicles (60–120 μg protein). The incubation is initiated by the addition of the BBMV while vortexing and the reaction is to be stopped by the addition of 5 ml of ice cold buffer (20 mM Hepes-tris, 150 mM KCl) followed immediately by filtration through a nylon filter (0.2 μm pore) and an additional 5 ml wash with stop buffer.

Measurement of Hepatic Cholesterol Concentration (HEPATIC CHOL)

Liver tissue is to be weighed and homogenized in chloroform:methanol (2:1). After homogenization and centrifugation the supernatant is separated and dried under nitrogen. The residue is to be dissolved in isopropanol and the cholesterol content will be measured enzymatically, using a combination of cholesterol oxidase and peroxidase, as described by Allain, C. A. et al., *Clin. Chem.*, 20, 470 (1974) (herein incorporated by reference).

Measurement of Hepatic HMG CoA-Reductase Activity (HMG COA)

Hepatic microsomes are to be prepared by homogenizing liver samples in a phosphate/sucrose buffer, followed by centrifugal separation. The final pelleted material is resuspended in buffer and an aliquot will be assayed for HMG CoA reductase activity by incubating for 60 minutes at 37° C. in the presence of $^{14}$C-HMG-CoA (Dupont-NEN). The reaction is stopped by adding 6N HCl followed by centrifugation. An aliquot of the supernatant is separated, by thin-layer chromatography, and the spot corresponding to the enzyme product is scraped off the plate, extracted and radioactivity is determined by scintillation counting. (Reference: Akerlund, J. and Bjorkhem, I. (1990) *J. Lipid Res.* 31, 2159).

Measurement of Hepatic Cholesterol 7-α-Hydroxylase Activity (7a-OHase)

Hepatic microsomes are to be prepared by homogenizing liver samples in a phosphate/sucrose buffer, followed by centrifugal separation. The final pelleted material is resuspended in buffer and an aliquot will be assayed for cholesterol 7-α-hydroxylase activity by incubating for 5 minutes at 37° C. in the presence of NADPH. Following extraction into petroleum ether, the organic solvent is evaporated and the residue is dissolved in acetonitrile/methanol. The enzymatic product will be separated by injecting an aliquot of the extract onto a $C_{18}$ reversed phase HPLC column and quantitating the eluted material using UV detection at 240 nm. (Reference: Horton, J. D., et al. (1994) *J. Clin. Invest.* 93, 2084).

Determination of Serum Cholesterol (SER.CHOL, HDL-CHOL, TGI and VLDL+LDL)

Total serum cholesterol (SER.CHOL) are to be measured enzymatically using a commercial kit from Wako Fine Chemicals (Richmond, Va.); Cholesterol C11, Catalog No. 276–64939. HDL cholesterol (HDL-CHOL) will be assayed using this same kit after precipitation of VLDL and LDL with Sigma Chemical Co. HDL Cholesterol reagent, Catalog No. 352–3 (dextran sulfate method). Total serum triglycerides (blanked) (TGI) will be assayed enzymatically with Sigma Chemical Co. GPO-Trinder, Catalog No. 337-B. VLDL and LDL (VLDL+LDL) cholesterol concentrations will be calculated as the difference between total and HDL cholesterol.

Measurement of Hamster Fecal Bile Acid Concentration (FBA)

Total fecal output from individually housed hamsters is to be collected for 24 or 48 hours, dried under a stream of nitrogen, pulverized and weighed. Approximately 0.1 gram is weighed out and extracted into an organic solvent (butanol/water). Following separation and drying, the residue is dissolved in methanol and the amount of bile acid present is measured enzymatically using the 3α-hydroxysteroid steroid dehydrogenase reaction with bile acids to reduce NAD. (Mashige, F. et al. *Clin. Chem.*, 27, 1352 (1981), herein incorporated by reference).

Dog Model for Evaluating Lipid Lowering Drugs

Male beagle dogs, obtained from a vendor such as Marshall farms and weighing 6–12 kg are fed once a day for two hours and given water ad libitum. Dogs may be randomly assigned to a dosing groups consisting of 6 to 12 dogs each, such as: vehicle, i.g.; 1 mg/kg, i.g.; 2 mg/kg, i.g.; 4 mg/kg, i.g.; 2 mg/kg, p.o. (powder in capsule). Intra-gastric dosing of a therapeutic material dissolved in aqueous solution (for example, 0.2% Tween 80 solution [polyoxyethylene monooleate, Sigma Chemical Co., St. Louis, Mo.]) may be done using a gavage tube. Prior to initiating dosing, blood samples may be drawn from the cephalic vein in the morning before feeding in order to evaluate serum cholesterol (total and HDL) and triglycerides. For several consecutive days animals are dosed in the morning, prior to feeding. Animals are to be allowed 2 hours to eat before any remaining food is removed. Feces are to be collected over a 2 day period at the end of the study and may be analyzed for bile acid or lipid content. Blood samples are also to be taken, at the end of the treatment period, for comparison with pre-study serum lipid levels. Statistical significance will be determined using the standard student's T-test with $p<.05$.

Dog Serum Lipid Measurement

Blood is to be collected from the cephalic vein of fasted dogs in serum separator tubes (Vacutainer SST, Becton Dickinson and Co., Franklin Lakes, N.J.). The blood is centrifuged at 2000 rpm for 20 minutes and the serum decanted.

Total cholesterol may be measured in a 96 well format using a Wako enzymatic diagnostic kit (Cholesterol CII) (Wako Chemicals, Richmond, Va.), utilizing the cholesterol oxidase reaction to produce hydrogen peroxide which is measured colorimetrically. A standard curve from 0.5 to 10 μg cholesterol is to be prepared in the first 2 columns of the plate. The serum samples (20–40 μl, depending on the expected lipid concentration) or known serum control samples are added to separate wells in duplicate. Water is added to bring the volume to 100 μl in each well. A 100 μl aliquot of color reagent is added to each well and the plates will be read at 500 nm after a 15 minute incubation at 37 degrees centigrade.

HDL cholesterol may be assayed using Sigma kit No. 352-3 (Sigma Chemical Co., St. Louis, Mo.) which utilizes dextran sulfate and Mg ions to selectively precipitate LDL and VLDL. A volume of 150 μl of each serum sample is to be added to individual microfuge tubes, followed by 15 μl of HDL cholesterol reagent (Sigma 352-3). Samples are to be mixed and centrifuged at 5000 rpm for 5 minutes. A 50 μl aliquot of the supernatant is to be then mixed with 200 μl of saline and assayed using the same procedure as for total cholesterol measurement.

Triglycerides are to be measured using Sigma kit No. 337 in a 96 well plate format. This procedure will measure glycerol, following its release by reaction of triglycerides with lipoprotein lipase. Standard solutions of glycerol (Sigma 339-11) ranging from 1 to 24 μg are to be used to generate the standard curve. Serum samples (20–40 μl, depending on the expected lipid concentration) are added to wells in duplicate. Water is added to bring the volume to 100 μl in each well and 100 μl of color reagent is also added to each well. After mixing and a 15 minute incubation, the plates will be read at 540 nm and the triglyceride values calculated from the standard curve. A replicate plate is also to be run using a blank enzyme reagent to correct for any endogenous glycerol in the serum samples.

Dog Fecal Bile Acid Measurement

Fecal samples may be collected to determine the fecal bile acid (FBA) concentration for each animal. Fecal collections may be made during the final 48 hours of the study, for two consecutive 24 hour periods between 9:00 am and 10:00 am each day, prior to dosing and feeding. The separate two day collections from each animal are to be weighed, combined and homogenized with distilled water in a processor (Cuisinart) to generate a homogeneous slurry. About 1.4 g of the homogenate is to be extracted in a final concentration of 50% tertiary butanol/distilled water (2:0.6) for 45 minutes in a 37° C. water bath and centrifuged for 13 minutes at 2000×g. The concentration of bile acids (mmoles/day) may be determined using a 96-well enzymatic assay system (1,2). A 20 μl aliquot of the fecal extract is to be added to two sets each of triplicate wells in a 96-well assay plate. A standardized sodium taurocholate solution and a standardized fecal extract solution (previously made from pooled samples and characterized for its bile acid concentration) will also analyzed for assay quality control. Twenty-microliter aliquots of sodium taurocholate, serially diluted to generate a standard curve are similarly to be added to two sets of triplicate wells. A 230 μl reaction mixture containing 1M hydrazine hydrate, 0.1 M pyrophosphate and 0.46 mg/ml NAD is to be added to each well. A 50 μl aliquot of 3a-hydroxysteroid-dehydrogenase enzyme (HSD; 0.8 units/ml) or assay buffer (0.1 M sodium pyrophosphate) are then added to one of the two sets of triplicates. All reagents may be obtained from Sigma Chemical Co., St. Louis, Mo. Following 60 minutes of incubation at room temperature, the optical density at 340 nm will be measured and the mean of each set of triplicate samples will be calculated. The difference in optical density±HSD enzyme is to be used to determine the bile acid concentration (mM) of each sample based on the sodium taurocholate standard curve. The bile acid concentration of the extract, the weight of the fecal homogenate (grams) and the body weight of the animal are to be used to calculate the corresponding FBA concentration in mmoles/kg/day for each animal. The mean FBA concentration (mmoles/kg/day) of the vehicle group is to be subtracted from the FBA concentration of each treatment group to determine the increase (delta value) in FBA concentration as a result of the treatment.

Plasma Lipids Assay in Rabbits

Plasma lipids can be assayed using standard methods as reported by J.R. Schuh et al., *J. Clin. Invest.*, 91, 1453–1458 (1993), herein incorporated by reference. Groups of male, New Zealand white rabbits are placed on a standard diet (100 g/day) supplemented with 0.3% cholesterol and 2% corn oil (Zeigler Bothers, Inc., Gardners, Pa.). Water is available ad lib. Groups of control and treated animals are killed after 1 and 3 months of treatment. Tissues are removed for characterization of atherosclerotic lesions. Blood samples are taken for determination of plasma lipid concentrations.

Plasma Lipids

Plasma for lipid analysis is obtained by withdrawing blood from the ear vein into EDTA-containing tubes (Vacutainer; Becton Dickenson & Co., Rutherford, N.J.), followed by centrifugal separation of the cells. Total cholesterol is determined enzymatically, using the cholesterol oxidase reaction (C. A. Allain et al., *Clin. Chem.*, 20, 470–475 (1974), herein incorporated by reference). HDL cholesterol is also measured enzymatically, after selective precipitation of LDL and VLDL by dextran sulfate with magnesium (G. R. Warnick et al., *Clin. Chem.*, 28, 1379-1388 (1982), herein incorporated by reference). Plasma triglyceride levels are determined by measuring the amount of glycerol released by lipoprotein lipase through an enzyme-linked assay (G. Bucolo et al., *Clin. Chem.*, 19, 476–482 (1973), herein incorporated by reference).

Atherosclerosis

Animals are killed by pentobarbital injection. Thoracic aortas are rapidly removed, immersion fixed in 10% neutral buffered formalin, and stained with oil red 0 (0.3%). After a single longitudinal incision along the wall opposite the arterial ostia, the vessels are pinned open for evaluation of the plaque area. The percent plaque coverage is determined from the values for the total area examined and the stained area, by threshold analysis using a true color image analyzer (Videometric 150; American Innovision, Inc., San Diego, Calif.) interfaced to a color camera (Toshiba 3CCD) mounted on a dissecting microscope. Tissue cholesterol will be measured enzymatically as described, after extraction with a chloroform/methanol mixture (2:1) according to the method of Folch et al. (*J. Biol. Chem.*, 226, 497–509 (1957), herein incorporated by reference).

In Vitro Vascular Response

The abdominal aortas are rapidly excised, after injection of sodium pentobarbital, and placed in oxygenated Krebs-bicarbonate buffer. After removal of perivascular tissue, 3-mm ring segments are cut, placed in a 37° C. muscle bath containing Krebs-bicarbonate solution, and suspended between two stainless steel wires, one of which is attached to a force transducer (Grass Instrument Co., Quincy, Mass.). Force changes in response to angiotensin II added to the bath will be recorded on a chart recorder.

CETP Activity Assay in Human Plasma (Tritiated Cholesteryl Ester)

Blood is to be obtained from healthy volunteers. Blood is collected in tubes containing EDTA (EDTA plasma pool). The EDTA human plasma pool previously stored at −20° C., is to be thawed at room temperature, and centrifuged for 5 minutes to remove any particulate matter. Tritiated HDL, radiolabeled in the cholesteryl ester moiety ([$^3$H]CE-HDL) as described by Morton and Zilversmit (*J. Biol. Chem.*, 256, 11992–95 (1981)), is to be added to the plasma to a final concentration of (25 $\mu$g/ml cholesterol). Inhibitor compounds are to be added to the plasma as follows: Equal volumes of the plasma containing the [$^3$H]CE-HDL (396 $\mu$l) are added by pipette into micro tubes (Titertube, Bio-Rad laboratories, Hercules, Calif.). Compounds, usually dissolved as 20–50 mM stock solutions in DMSO, are to be serially diluted in DMSO (or an alternative solvent in some cases, such as dimethylformamide or ethanol). Four $\mu$l of each of the serial dilutions of inhibitor compounds or DMSO alone are then added to each of the plasma tubes. The tubes are immediately mixed. Triplicate aliquots (100 $\mu$l) from each plasma tube are then transferred to wells of 96-well round-bottomed polystyrene microtiter plates (Corning, Corning, N.Y.). Plates are sealed with plastic film and incubated at 37° C. for 4 hours. Test wells are to contain plasma with dilutions of inhibitor compounds. Control wells are to contain plasma with DMSO alone. Blank wells are to contain plasma with DMSO alone that are left in the micro tubes at 4° C. for the 4 hour incubation and are added to the microtiter wells at the end of the incubation period. VLDL and LDL are precipitated by the addition of 10 $\mu$l of precipitating reagent (1% (w/v) dextran sulfate (Dextralip50)/0.5 M magnesium chloride, pH 7.4) to all wells. The wells are mixed on a plate mixer and then incubated at ambient temperature for 10 min. The plates are then centrifuged at 1000×g for 30 min at 10° C. The supernatants (50 $\mu$l) from each well are then transferred to Picoplate™ 96 plate wells (Packard, Meriden, Conn.) containing 250:1 Microscint™-40 (Packard, Meriden, Conn.). The places are heat-sealed (TopSeal™-P, Packard, Meriden, Conn.) according to the manufacturer's directions and mixed for 30 min. Radioactivity will be measured on a microplate scintillation counter (TopCount, Packard, Meriden, Conn.). IC$_{50}$ values will be determined as the concentration of inhibitor compound inhibiting transfer of [$^3$H]CE from the supernatant [$^3$H]CE-HDL to the precipitated VLDL and LDL by 50% compared to the transfer obtained in the control wells. The maximum percentage transfer (in the control wells) will be determined using the following equation:

$$\% \text{ Transfer} = \frac{[dpm_{blank} - dpm_{control}] \times 100}{dpm_{blank}}$$

The percentage of control transfer determined in the wells containing inhibitor compounds is determined as follows:

$$\% \text{ Control} = \frac{[dpm_{blank} - dpm_{test}] \times 100}{dpm_{blank} - dpm_{control}}$$

IC$_{50}$ values will be calculated from plots of % control versus concentration of inhibitor compound.

CETP Activity In Vitro

The ability of compounds to inhibit CETP activity are assessed using an in vitro assay that measures the rate of transfer of radiolabeled cholesteryl ester ([$^3$H]CE) from HDL donor particles to LDL acceptor particles. Details of the assay are provided by Glenn et al. (Glenn and Melton, "Quantification of Cholesteryl Ester Transfer Protein (CETP): A) CETP Activity and B) Immunochemical Assay of CETP Protein," *Meth. Enzymol.*, 263, 339–351 (1996)). CETP can be obtained from the serum-free conditioned medium of CHO cells transfected with a cDNA for CETP (Wang, S. et al. *J. Biol. Chem.* 267, 17487–17490 (1992)). To measure CETP activity, [$^3$H]CE-labeled HDL, LDL, CETP and assay buffer (50 mM tris(hydroxymethyl) aminomethane, pH 7.4; 150 mM sodium chloride; 2 mM ethylenediamine-tetraacetic acid; 1% bovine serum albumin) are incubated in a volume of 200 $\mu$l, for 2 hours at 37° C. in 96 well plates. LDL is differentially precipitated by the addition of 50 $\mu$l of 1% (w/v) dextran sulfate/0.5 M magnesium chloride, mixed by vortex, and incubated at room temperature for 10 minutes. The solution (200 $\mu$l) is transferred to a filter plate (Millipore). After filtration, the radioactivity present in the precipitated LDL is measured by liquid scintillation counting. Correction for non-specific transfer or precipitation is made by including samples that do not contain CETP. The rate of [$^3$H]CE transfer using this assay is linear with respect to time and CETP concentration, up to 25–30% of [$^3$H]CE transferred.

The potency of test compounds can be determined by performing the above described assay in the presence of varying concentrations of the test compounds and determining the concentration required for 50% inhibition of transfer of [$^3$H]CE from HDL to LDL. This value is defined as the IC$_{50}$. The IC$_{50}$ values determined from this assay are accurate when the IC$_{50}$ is greater than 10 nM. In the case where compounds have greater inhibitory potency, accurate measurements of IC$_{50}$ may be determined using longer incubation times (up to 18 hours) and lower final. concentrations of CETP (<50 nM).

Inhibition of CETP Activity In Vivo

Inhibition of CETP activity by a test compound can be determined by administering the compound to an animal by intravenous injection or oral gavage, measuring the amount of transfer of tritium-labeled cholesteryl ester ([$^3$H]CE) from HDL to VLDL and LDL particles, and comparing this amount of transfer with the amount of transfer observed in control animals.

Male golden Syrian hamsters are maintained on a diet of chow containing 0.24% cholesterol for at least two weeks prior to the study. For animals receiving intravenous dosing, immediately before the experiment, animals are anesthetized with pentobarbital. Anesthesia is maintained throughout the experiment. In-dwelling catheters are inserted into the jugular vein and carotid artery. At the start of the experiment all animals will receive 0.2 ml of a solution containing [$^3$H]CE-HDL into the jugular vein. [$^3$H]CE-HDL is a preparation of human HDL containing tritium-labeled cholesteryl ester, and is prepared according to the method of Glenn et al. (*Meth. Enzymol.*, 263, 339–351 (1996)). Test compound is dissolved as a 80 mM stock solution in vehicle (2% ethanol: 98% PEG 400, Sigma Chemical Company, St. Louis, Mo. USA) and administered either by bolus injection or by continuous infusion. Two minutes after the [$^3$H]CE-HDL dose is administered, animals receive 0.1 ml of the test solution injected into the jugular vein. Control animals receive 0.1 ml of the intravenous vehicle solution without test compound. After 5 minutes, the first blood samples (0.5 ml) are taken from the carotid artery and collected in standard microtainer tubes containing ethylenediamine tetraacetic acid. Saline (0.5 ml) is injected to flush the catheter and replace blood volume. Subsequent blood samples are taken at two hours and four hours bag the same method. Blood samples are mixed well and kept on ice until the completion of the experiment. Plasma is obtained by centrifugation of the blood samples at 40° C. The plasma (50 $\mu$l) is treated with 5 $\mu$l of precipitating reagent (dextran sulfate, 10 g/l; 0.5 M magnesium chloride) to remove VLDL/LDL. After centrifugation, the resulting supernatant (25 $\mu$l) containing the HDL is analyzed for radioactivity using a liquid scintillation counter.

The percentage [$^3$H]CE transferred from HDL to LDL and VLDL (% transfer) is calculated based on the total radioactivity in equivalent plasma samples before precipitation. Typically, the amount of transfer from HDL to LDL and VLDL in control animals is 20% to 35% after 4 hours.

Alternatively, conscious, non-anesthetized animals can receive an oral gavage dose of test compound as a suspension in 0.1% methyl cellulose in water. At a time determined for each compound at which plasma levels of the test substance reach their peak ($C_{max}$) after oral dosing, the animals are anesthetized with pentobarbital and then dosed with 0.2 ml of a solution containing [$^3$H]CE-HDL into the jugular vein as described above. Control animals receive 0.25 ml of the vehicle solution without test compound by oral gavage. After 4 hours, the animals are sacrificed, blood samples are collected, and the percentage [$^3$H]CE transferred from HDL to LDL and VLDL (% transfer) is assayed as described above.

Alternatively, inhibition of CETP activity by a test compound can be determined by administering the compound to mice that have been selected for expression of human CETP (hCETP) by transgenic manipulation (hCETP mice). Test compounds can be administered by intravenous injection, or oral gavage and the amount of transfer of tritium-labeled cholesteryl ester ([$^3$H]CE) from HDL to VLDL and LDL particles is determined, and compared to the amount of transfer observed in control animals. C57Bl/6 mice that are homozygous for the hCETP gene are maintained on a high fat chow diet, such as TD 88051, as described by Nishina et al. (*J Lipid Res.*, 31, 859–869 (1990)) for at least two weeks prior to the study. Mice receive an oral gavage dose of test compound as a suspension in 0.1% methyl cellulose in water or an intravenous bolus injection of test compound in 10% ethanol and 90% polyethylene glycol. Control animals receive the vehicle solution without test compound by oral gavage or by an intravenous bolus injection. At the start of the experiment all animals receive 0.05 ml of a solution containing [$^3$H]CE-HDL into the tail vein. [$^3$H]CE-HDL is a preparation of human HDL containing tritium-labeled cholesterol ester, and is prepared according to the method of Glenn et al. (*Meth. Enzymol.*, 263, 339–351 (1996)). After 30 minutes, the animals are exsanguinated and blood collected in standard microtainer tubes containing ethylenediamine tetraacetic acid. Blood samples are mixed well and kept on ice until the completion of the experiment. Plasma is obtained by centrifugation of the blood samples at 40° C. The plasma is separated and analyzed by gel filtration chromatography and the relative proportion of [$^3$H]CE in the VLDL, LDL and HDL regions is determined.

The percentage [$^3$H]CE transferred from HDL to LDL and VLDL (% transfer) is calculated based on the total radioactivity in equivalent plasma samples before precipitation. Typically, the amount of transfer from HDL to LDL and VLDL in control animals is 20% to 35% after 30 min.

Intestinal Cholesterol Absorption Assay

A variety of compounds are shown to inhibit cholesterol absorption from the intestinal tract. These compounds lower serum cholesterol levels by reducing intestinal absorption of cholesterol from both exogenous sources (dietary cholesterol) and endogenous cholesterol (secreted by the gall bladder into the intestinal tract).

In hamsters the use of a dual-isotope plasma ratio method to measure intestinal cholesterol absorption has been refined and evaluated as described by Turley et al. (J. Lipid Res. 35, 329–339 (1994), herein incorporated by reference).

Male hamsters weighing 80–100 g are given food and water ad libitum in a room with 12 hour alternating periods of light and dark. Four hours into the light period, each hamster is administered first an intravenous dose of 2.5 $\mu$Ci of [1,2-$^3$H]cholesterol suspended in Intralipid (20%) and then an oral dose of [4-$^{14}$C]cholesterol in an oil of medium chain triglycerides (MCT). The i.v. dose is given by injecting a 0.4 ml volume of the Intralipid mixture into the distal femoral vein. The oral dose is given by gavaging a 0.6 ml volume of the MCT oil mixture introduced intragastrically via a polyethylene tube. After 72 hours the hamsters are bled and the amount of $^3$H and $^{14}$C in the plasma and in the original amount of label administered are determined by liquid scintillation spectrometry. The cholesterol absorption will be calculated based on the following equation:

Percent cholesterol absorbed =

$$\frac{\% \text{ of oral dose } per \text{ ml of 72 hour plasma sample}}{\% \text{ of } i.v. \text{ dose per ml of 72 hour plasma sample}} \times 100$$

The examples herein can be performed by substituting the generically or specifically described therapeutic compounds or inert ingredients for those used in the preceding examples.

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A therapeutic combination comprising a first amount of an ileal bile acid transport (IBAT) inhibiting compound and a second amount of a cholesteryl ester transfer protein (CETP) inhibiting compound wherein the first amount and the second amount together comprise an anti-hyperlipidemic condition effective amount, an anti-atherosclerotic condition effective amount, or an anti-hypercholesterolemic condition effective amount of the compounds, and wherein said cholesteryl ester transfer protein inhibiting compound comprises compound C-12 represented by:

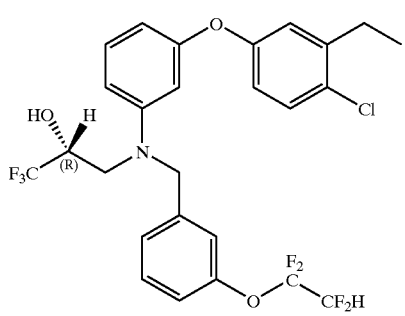

(C-12)

or enantiomers or racemates thereof.

2. A therapeutic combination comprising a first amount of an ileal bile acid transport (IBAT) inhibiting compound and a second amount of a cholesteryl ester transfer protein (CETP) inhibiting compound wherein the first amount and the second amount together comprise an anti-hyperlipidemic condition effective amount, an anti-atherosclerotic condition effective amount, or an anti-hypercholesterolemic condition effective amount of the compounds, wherein said cholesteryl ester transfer protein inhibiting compound comprises compound C-12 represented by:

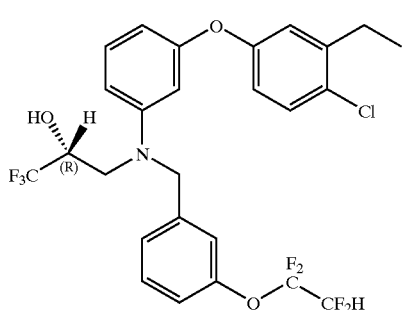

(C-12)

or enantiomers or racemates thereof, and wherein said ileal bile acid transport inhibiting compound comprises compound B-5 represented by:

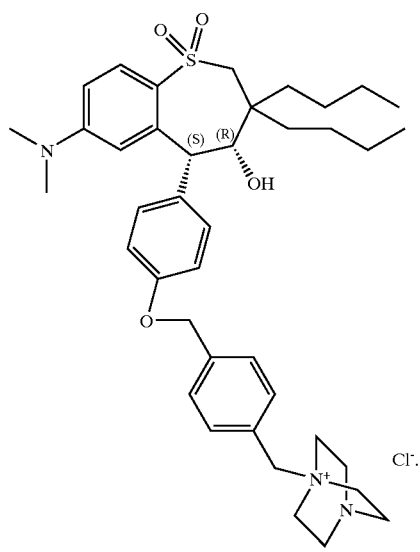

(B-5)

or enantiomers or racemates thereof.

3. The therapeutic combination of claim 1, wherein said ileal bile acid transport inhibiting compound comprises compound B-5 represented by:

(B-5)

4. The therapeutic combination of claim 1, wherein said cholesteryl ester transfer protein inhibiting compound comprises compound C-12 represented by:

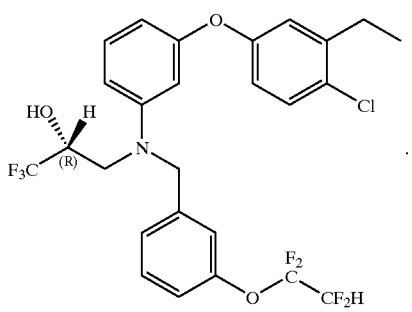

5. The therapeutic combination of claim 4, wherein said ideal bile acid transport inhibiting compound comprises compound B-5 represented by:

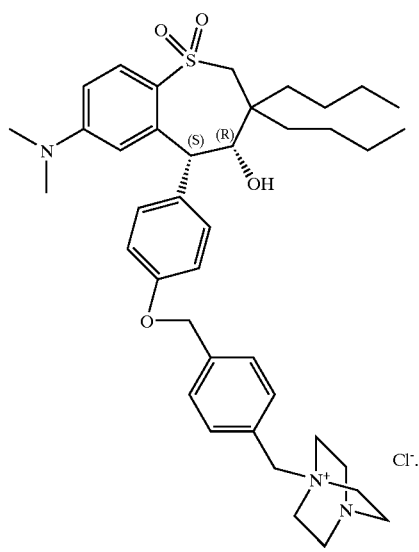

6. A method for the prophylaxis or treatment of a hyperlipidemic condition comprising administering to a patient in need thereof a combination in unit dosage form wherein the combination comprises a first amount of an ileal bile acid transport inhibiting compound and a second amount of a cholesteryl ester transfer protein inhibiting compound wherein the first amount and the second amount together comprise an anti-hyperlipidemic condition effective amount of the compounds, and wherein said cholesteryl ester transfer protein inhibiting compound is represented by formula (C-12):

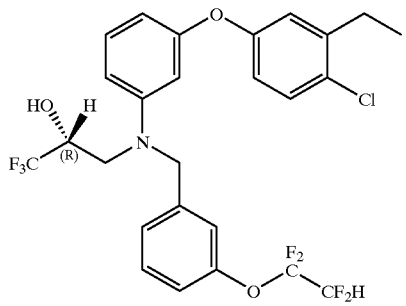

or enantiomers or racemates thereof.

7. A method for the prophylaxis or treatment of an atherosclerotic condition comprising administering to a patient in need thereof a combination in unit dosage form wherein the combination comprises a first amount of an ileal bile acid transport inhibiting compound and a second amount of a cholesteryl ester transfer protein inhibiting compound wherein the first amount and the second amount together comprise an anti-atherosclerotic condition effective amount of the compounds, and wherein said cholesteryl ester transfer protein inhibiting compound is represented by formula (C-12):

or enantiomers or racemates thereof.

8. A method for the prophylaxis or treatment of hypercholesterolemia comprising administering to a patient in need thereof a combination in unit dosage form wherein the combination comprises a first amount of an ileal bile acid transport inhibiting compound and a second amount of a cholesteryl ester transfer protein inhibiting compound wherein the first amount and the second amount together comprise an anti-hypercholesterolemic condition effective amount of the compounds, and wherein said cholesteryl ester transfer protein inhibiting compound is represented by formula (C-12):

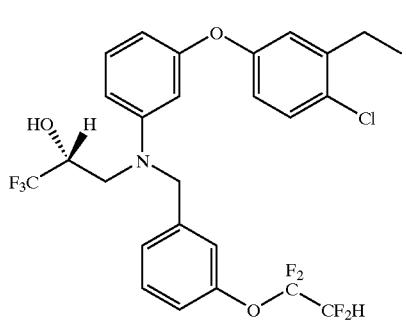

or enantiomers or racemates thereof.

* * * * *